(12) United States Patent
Ilan

(10) Patent No.: US 11,116,658 B2
(45) Date of Patent: Sep. 14, 2021

(54) DEVICES FOR GASTROINTESTINAL STIMULATION AND USES THEREOF

(71) Applicant: OBERON SCIENCES ILAN LTD., Kfar Tavor (IL)

(72) Inventor: Yaron Ilan, Kefar Tavor (IL)

(73) Assignee: OBERON SCIENCES ILAN LTD., Kfar Tavor (IL)

( * ) Notice: Subject to any disclaimer, the term of this patent is extended or adjusted under 35 U.S.C. 154(b) by 900 days.

(21) Appl. No.: 15/738,344

(22) PCT Filed: Jun. 22, 2016

(86) PCT No.: PCT/IL2016/050666
§ 371 (c)(1),
(2) Date: Dec. 20, 2017

(87) PCT Pub. No.: WO2017/002104
PCT Pub. Date: Jan. 5, 2017

(65) Prior Publication Data
US 2018/0185238 A1    Jul. 5, 2018

Related U.S. Application Data

(60) Provisional application No. 62/185,628, filed on Jun. 28, 2015.

(51) Int. Cl.
*A61F 7/12* (2006.01)
*A61H 9/00* (2006.01)
(Continued)

(52) U.S. Cl.
CPC .............. *A61F 7/12* (2013.01); *A61H 9/0078* (2013.01); *A61H 11/00* (2013.01); *A61H 23/004* (2013.01);
(Continued)

(58) Field of Classification Search
CPC ......... A61F 7/12; A61H 9/0078; A61H 11/00; A61H 23/02; A61H 23/004; A61N 1/36007
See application file for complete search history.

(56) References Cited

U.S. PATENT DOCUMENTS 5,724,996 A    3/1998  Piunti
5,993,473 A   11/1999  Chan et al.
(Continued)

FOREIGN PATENT DOCUMENTS

CA        2616101      2/2007
CN     101495173 A     7/2009
(Continued)

OTHER PUBLICATIONS

Abel, et al (2003) Gastric Electrical Stimulation for Medically Refractory Gastroparesis, Gastroenterology, 125: 421-428.
(Continued)

*Primary Examiner* — Timothy A Stanis
(74) *Attorney, Agent, or Firm* — The Roy Gross Law Firm, LLC; Roy Gross

(57) ABSTRACT

A gastrointestinal stimulation devices including a random stimulation delivery mechanism(s), configured to provide stimuli to a bodily tissue in a vicinity of the stimulation capsule, the provided random stimuli being characterized by a stimulation parameter, and a control circuitry in communication with said physical stimulation delivery mechanism, and configured to set and alter the stimulation parameter non-systematically, thereby altering the characterization of the stimuli provided to the bodily tissue. The algorithm may be patient tailored, and may have a learning machinery which responds to data being received from the patient.

19 Claims, 11 Drawing Sheets

(51) Int. Cl.
*A61H 23/02* (2006.01)
*A61N 1/04* (2006.01)
*A61N 1/36* (2006.01)
*A61H 23/00* (2006.01)
*A61H 11/00* (2006.01)
*A61N 1/375* (2006.01)
*A61N 1/05* (2006.01)
*A61N 2/00* (2006.01)
*A61F 7/00* (2006.01)
*A61H 15/00* (2006.01)
*A61F 7/02* (2006.01)

(52) U.S. Cl.
CPC ......... *A61H 23/02* (2013.01); *A61H 23/0218* (2013.01); *A61N 1/0509* (2013.01); *A61N 1/36002* (2017.08); *A61N 1/36007* (2013.01); *A61N 1/36034* (2017.08); *A61N 1/3756* (2013.01); *A61F 7/00* (2013.01); *A61F 2007/0022* (2013.01); *A61F 2007/0093* (2013.01); *A61F 2007/0094* (2013.01); *A61F 2007/0095* (2013.01); *A61F 2007/0228* (2013.01); *A61H 15/00* (2013.01); *A61H 2011/005* (2013.01); *A61H 2015/0042* (2013.01); *A61H 2023/0209* (2013.01); *A61H 2201/0103* (2013.01); *A61H 2201/0207* (2013.01); *A61H 2201/0214* (2013.01); *A61H 2201/0228* (2013.01); *A61H 2201/1207* (2013.01); *A61H 2201/165* (2013.01); *A61H 2201/1685* (2013.01); *A61H 2201/501* (2013.01); *A61H 2201/5007* (2013.01); *A61H 2201/5012* (2013.01); *A61H 2201/5035* (2013.01); *A61H 2201/5082* (2013.01); *A61H 2205/02* (2013.01); *A61H 2205/04* (2013.01); *A61H 2205/06* (2013.01); *A61H 2205/083* (2013.01); *A61H 2230/08* (2013.01); *A61H 2230/70* (2013.01); *A61H 2230/705* (2013.01); *A61H 2230/80* (2013.01); *A61H 2230/805* (2013.01); *A61N 1/36053* (2013.01); *A61N 1/36139* (2013.01); *A61N 2/006* (2013.01)

(56) References Cited

U.S. PATENT DOCUMENTS

| | | | |
|---|---|---|---|
| 6,453,199 | B1 | 9/2002 | Kobozev |
| 7,824,347 | B2 | 11/2010 | Imran et al. |
| 8,295,932 | B2 | 10/2012 | Bitton et al. |
| 2004/0143182 | A1* | 7/2004 | Kucera .......... A61B 5/073 600/424 |
| 2005/0209653 | A1 | 9/2005 | Herbert et al. |
| 2006/0111632 | A1 | 5/2006 | Chen |
| 2006/0270899 | A1 | 11/2006 | Amirana |
| 2006/0276844 | A1 | 12/2006 | Alon et al. |
| 2007/0123809 | A1 | 5/2007 | Weiss et al. |
| 2007/0203521 | A1 | 8/2007 | Dobak et al. |
| 2007/0238940 | A1 | 10/2007 | Amirana |
| 2008/0033569 | A1 | 2/2008 | Ferren et al. |
| 2008/0077192 | A1 | 3/2008 | Harry et al. |
| 2008/0275430 | A1 | 11/2008 | Belsky et al. |
| 2009/0030473 | A1* | 1/2009 | Khawaled .......... A61N 1/36007 607/40 |
| 2009/0306633 | A1* | 12/2009 | Trovato .......... A61B 5/036 604/891.1 |
| 2009/0318841 | A1 | 12/2009 | Shohat et al. |
| 2010/0023132 | A1 | 1/2010 | Imran |
| 2012/0046579 | A1 | 2/2012 | Radl et al. |
| 2012/0165855 | A1 | 6/2012 | Shalon et al. |
| 2015/0051589 | A1* | 2/2015 | Sako .......... A61M 31/002 604/891.1 |
| 2015/0127077 | A1 | 5/2015 | Ben Asher et al. |

FOREIGN PATENT DOCUMENTS

| | | |
|---|---|---|
| CN | 101516314 A | 8/2009 |
| JP | 2001-0523491 | 11/2001 |
| JP | 2004-538055 | 12/2004 |
| JP | 2015-515906 | 6/2005 |
| JP | 2008-500086 | 1/2008 |
| JP | 2008-509794 | 4/2008 |
| JP | 2010-503451 | 2/2010 |
| JP | 2011-524782 | 9/2011 |
| JP | 2012-210375 | 11/2012 |
| JP | 5145102 | 11/2012 |
| WO | 3925418 A1 | 5/1999 |
| WO | 2003001966 A2 | 1/2003 |
| WO | 2004037071 | 5/2004 |
| WO | 2005115536 A1 | 12/2005 |
| WO | 2006023498 A1 | 3/2006 |
| WO | 2006131522 | 12/2006 |
| WO | 2009154459 A2 | 12/2009 |
| WO | 2010128495 | 11/2010 |
| WO | 2012132516 A1 | 10/2012 |
| WO | 2013121276 | 8/2013 |
| WO | 2013168168 A1 | 11/2013 |

OTHER PUBLICATIONS

Benamouzig, et al (2013) Effects of Intragastric Balloon on Weight Loss, Physical Activity, Plasma Leptin and Ghrelin in Obese Patients, with Long-Term Follow-Up, Journal of GHR, 2(8): 744-749.

Borovikova, et al (2000) Vagus nerve stimulation attenuates the systemic inflammatory response to endotoxin, Nature 405 (6785): 458-62.

Bortolotti, Mauro (2011) Gastric electrical stimulation for gastroparesis: A goal greatly pursued, but not yet attained, World J Gastroenterol, 17(3): 273-282.

Brown, et al (1995) Validity and epidemiology of reported poor appetite among Peruvian infants from a low-income, periurban community, Am J Clin Nutr, 61: 26-32.

De Silva, et al (2012) Gut Hormones and Appetite Control: A Focus on PYY and GLP-1 as Therapeutic Targets in Obesity, Gut and Liver, 6(1): 10-20.

Dogan, et al (2013) Five Percent Weight Lost in the First Month of Intragastric Balloon Treatment May Be a Predictor for Long-Term Weight Maintenance, Obes Surg, 23:1727-1733.

Ghia, et al (2008) Impaired parasympathetic function increases susceptibility to inflammatory bowel disease in a mouse model of depression, J Clin Invest, 118: 2209-2218.

Ghia, etal (2006) The Vagus Nerve: A Tonic Inhibitory Influence Associated With Inflammatory Bowel Disease in a Murine Model, Gastroenterology, vol. 131,1122-1130.

Giuricin, et al (2012) Short- and Long-Term Efficacy of Intragastric Air-Filled Balloon (Heliosphere BAG) Among Obese Patients, Obes Surg, 22(11): 1686-9.

GroupHealth, Clinical Review Criteria, Gastric Electric stimulation for the treatment of medically refractory diabetic gastroparesis.

Harvard Pilgrim HealthCare (2012) ,Gastric Electrical Stimulation (GES) for Gastroparesis and Obesity.

Hussain, et al (2013) The Regulation of food intake by the gut-brain axis: implications for obesity, International Journal of Obesity, 37: 625-633.

Ludy, et al (2012) The Effects of Capsaicin and Capsiate on Energy Balance: Critical Rev and Meta-analysis of Studies in Humans, Chem Senses 37: 103-121.

McConnachie, et al (2004) The effect of temperature on digestive assimilation efficiency, gut passage time and appetite in an ambush foraging lizard, Cordylus melanotus melanotus, J Comp Physiol B, 174: 99-105.

McKenna, et al (2008) Gastric electrical stimulation is an effective and safe treatment for medically refractory gastroparesis, Surgery, 144(4): 566-572.

Medical Advisory Secretariat (2006) Gastric Electrical Stimulation: An Evidence-Based Analysis, Ontario Health Technology Assessment Series 6(16).

(56) References Cited

OTHER PUBLICATIONS

Meregnani, et al (2010) Anti-inflammatory effect of vagus nerve stimulation in a rat model of inflammatory bowel disease, Autonomic Neuroscience: Basic and Clinical, 160: 82-89.

Mizrahi, et al (2012) Gastric stimulation for weight loss, World Journal of Gastroenterology, 18(19): 2309-2319.

Moga, et al (2006) Gastric Electrical Stimulation (Enterra Therapy System for the Treatment of Gastroparesis, Alberta Heritage Foundation for Medical Research.

O'Grady, et al (2009) High-Frequency Gastric Electrical Stimulation for the Treatment of Gastroparesis: A Meta-Analysis, World J Surg, 33: 1693-1701.

Otis, et al (2011) Cholecystokinin activation of central satiety centers changes seasonally in a mammalian hibernator, General and Comparative Endocrinology, 171: 269-274.

Proulx, et al (2005) Mechanisms of oleoylethanolamide-induced changes in feeding behavior and motor activity, Am J Physiol Regul Integr Comp Physiol 289, R729-R737.

Rao, et al (2007) The Bioenteric Intragastric Balloon (BIB) as a treatment for obesity: poor results in Asian patients, Singapore Med J, 48(3): 227-231.

Saeed, et al (2014) Changes in levels of peripheral hormones controlling appetite are inconsistent with hyperphagia in leptin-deficient subjects, Endorcrine, 45: 401-408.

Saruc, et al (2010) Intragastric balloon treatment of obesity must be combined with bariatric surgery: A pilot study in Turkey, Turk J Gastroenterol, 21 (4): 333-337.

Sauer, et al (2013) A New Endoscopically Implantable Device (SatiSphere) for Treatment of Obesity—Efficacy, Safety, and Metabolic Effects on Glucose, Insulin, and GLP-1 Levels, Obes Surg 23: 1727-1733.

Scott, et al (2013), Gut Hormones and Obesity: Physiology and Therapies, Vitam Horm, 91: 143-194.

Suzuki, et al (2011) The Gut Hormones in Appetite Regulation, J Obes, 528401.

Suzuki, et al, (2012) Obesity and Appetite Control, Experimental Diabetes Research, 824305.

Tan et al (2013) Gut hormones as therapeutic agents in treatment of diabetes and obesity, Current Opinion in Pharmacology, 13: 996-1001.

Tan, et al (2013) Coadministration of Glucagon-Like Peptide-1 During Glucagon Infusion in Humans Results in Increased Energy Expenditure and Amelioration of Hyperglycemia, Diabetes, 62(4): 1131-1138.

Torii, et al (2013) Physiological roles of dietary glutamate signaling via gut-brain axis due to efficient digestion and absorption, J Gastroenteral 48: 442-451.

Troke, et al (2013) The future role of gut hormones in the treatment of obesity, Ther Adv Chronic Dis, 5(1): 4-14.

PCT Search Report for International Application No. PCT/IL2016/050666 dated Oct. 13, 2016, 5 pp.

PCT Written Opinion for International Application No. PCT/IL2016/050666 dated Oct. 13, 2016, 4 pp.

PCT International Preliminary Report on Patentability for International Application No. PCT/IL2016/050666, dated Jan. 2, 2018, 5 pp.

\* cited by examiner

DEVICES FOR GASTROINTESTINAL STIMULATION AND USES THEREOF

RELATED APPLICATIONS

This application is a National Phase of PCT Patent Application No. PCT/IL2016/050666 having International filing date of Jun. 22, 2016, which claims the benefit of priority of U.S. Provisional Application No. 62/185,628 filed on Jun. 28, 2015 entitled DEVICES FOR GASTROINTESTINAL STIMULATION AND USES THEREOF. The contents of the above applications are all incorporated by reference as if fully set forth herein in their entirety.

FIELD

The present disclosure relates to medical devices configured to stimulate the gastrointestinal tract and optionally other organs through various stimuli including mechanical and electrical stimuli for prevention of the adaptation of the human body to regular stimuli.

BACKGROUND

The gut-brain axis is a bidirectional neuro-humoral communication system that integrates brain and gastrointestinal (GI) functions. The gut-brain axis is involved in a multitude of physiological processes including, for example, satiety, food intake, regulation of glucose and fat metabolism, and insulin secretion. In addition, a growing body of research shows that a gut-body communication axis also exists, where the gut affects various bodily functions through neuro- and hormonal pathways.

The vagus nerve, through its afferents and efferents, is thought to be one of the major conduits in these communication systems. For example, it has been shown that the vagus nerve is involved in anti-inflammatory responses. Studies have demonstrated that stimulation of the left cervical vagus nerve trunk (in the neck) using an electrode in various experimental models of inflammation results in anti-inflammatory. These effects are thought to be mediated via peripheral release of acetylcholine from the vagus and subsequent activation of macrophages.

With respect to appetite and satiety, the alimentary canal and its content are known to play a key role in mediating signals involved in appetite and satiety control. For example, intrinsic and extrinsic sensory neurons in the alimentary canal provide information about visceral distension (which generally corresponds to the volume of luminal contents), the chemical composition and temperature of ingested material and its movement along the mucosal surface of the gut. This input generates signals that regulate intestinal motility, blood flow, secretion and absorption, and is critical for normal digestion. In addition, hormones secreted from the gut or other organs, such as the pancreas, in response to the nutritional status of the body are involved in appetite and satiety control.

Manipulation of the gut-brain axis was previously suggested as a mean to control appetite and food absorption. Manipulation of the gut-brain axis was also suggested as a mean to control gastrointestinal (GI) motility. It was shown that mechanical stimulation applied to the walls of the GI tract or a segment thereof, for example, to the walls of the stomach, can affect processes regulated in the digestive system and can be used to induce such manipulations.

For example, gastric and intestinal electrical stimulation has been suggested for treating obesity and gastrointestinal dysmotility disorders, using implantable gastric pacemakers. The electrical stimulation is typically delivered by means of electrodes, implanted for example in the musculature of the gastric wall, which are connected to a stimulator device placed subcutaneously in the abdomen. For the treatment of gastric dysmotility, the device is typically set to deliver electrical pulses to the gastric and/or intestinal muscles with the objective of stimulating gastrointestinal myoelectric activity, and thereby alter the motility of the gastrointestinal tract. In the treatment for obesity, the goal of gastric stimulation is usually to cause early satiety and reduce appetite through electrical stimulation of the gastric wall, intestines or vagal nerve. It has been suggested that the pacemaker induces alterations in the secretion of hormones associated with hunger or satiety.

Another example is intragastric balloons, which are liquid-filled or air-filled balloons placed endoscopically in the stomach of patients and left inflated for six months.

There is thus a need for more effective means to stimulate different parts of the GI tract and optionally other body organs. For example, it would be highly beneficial to have an external device or an ingestible device having an optimized combination of stimulation capabilities together with means of control, that may be utilized to achieve long term, durable effects in various clinical applications relating to the digestive system, as well as in clinical conditions involving body parts outside the digestive system.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other advantages or improvements.

For some symptoms, it has been found that applying/providing stimulation to target regions in the human body may be utilized for affecting a treatment or for managing the symptom. Such stimulations may be mechanical, electrical and/or thermal, and can be provided by certain stimulation pattern such as pulses, alternating waves or other patterns.

The human body and other organisms have mechanisms of habituation, which is a form of learning in which the organism decreases or ceases to respond to the stimulus after repeated presentations. Essentially, the organism learns to decrease the response, or even stop responding to the stimulus, which renders the stimulation biologically irrelevant or less relevant.

As a result, applying stimuli utilizing repetitive patterns may result in having the target organ be less responsive to the stimulation treatment, thereby reducing the treatment efficacy.

The present disclosure provides, according to some aspects, medical devices capable of stimulating a target organ, such as the gastrointestinal tract, and their use for the treatment of various clinical conditions for overcoming the adaptation of human organs to procedures. Advantageously, the devices disclosed herein are configured to alter parameters of the stimulation during their operation, according to some embodiments; the disclosed herein are configured to randomly alter parameters of the stimulation during their operation. Moreover, most organs in the human body work according to a regular pattern. Regular pattern, such as regular electrical, endocrinological, cytokine patterns, or any other type of pattern, are associated with the habituation of the body organs. Irregular chaotic pattern is suggested to affect this habituation.

Without wishing to be bound by any particular theory of a mechanism of action, it is contemplated that the random (chaotic) dynamics of the stimulation applied by the devices of the present disclosure are configured such that to avoid/mitigate adaptation and/or accommodation of the body/target organ to the delivered stimuli, which may prevent their effect and/or reduce responsiveness over time. The random dynamics of the stimulation enables a sustained, prolonged effect on the target organ, and according to some embodiments, aid in preventing weight regain, or providing other treatment effects.

Advantageously, altering the stimuli parameters may reduce and/or prevent the habituation from occurring in the target organ, thereby increase the efficacy of the provided treatment. According to some embodiments, altering the stimuli parameters may be done randomly, or pseudo-randomly in a chaotic way.

According to some embodiments, the stimulation parameters may include frequencies, intermittencies, amplitude, alteration, shape of the stimuli signal, rise slope, fall slope and the like. A random chaotic combination of several types of stimulations, such as electrical, thermal, and like that, may further prevent the adaptation of the target organ to stimuli.

In some embodiments, gastrointestinal (GI) stimulation capsules or external wearable devices such as belts are provided, such as swallowable capsules that propel along the GI tract of a subject after they are swallowed and apply stimuli, e.g. mechanical and/or electrical stimuli, or any other type of stimuli, to the walls of the gastrointestinal tract. In other embodiments, external devices are provided, such as belts, which induce various stimuli from the outside.

In some embodiments, the present disclosure provides methods for treating diseases, including for example inflammatory and infectious diseases, using the devices disclosed herein. The present disclosure discloses that systemic beneficial effects induced by such devices can be utilized for the treatment of various diseases, including diseases affecting organs and body parts outside the digestive system. In some exemplary embodiments, the present disclosure discloses the use of gastrointestinal capsules in the treatment of inflammatory, infectious, autoimmune and malignant diseases or disorders.

According to some embodiments, the present disclosure discloses the use of gastrointestinal capsules for enhancing a function and/or condition in the body of the user, even if the user is not diseased.

The present disclosure provides, according to some embodiments, gastrointestinal stimulation capsules or belts which may be particularly useful for efficient treatment of gastrointestinal motility disorders and/or obesity, and may also be used for the treatment of other diseases or disorders. The improved gastrointestinal capsules and belts disclosed herein are configured to apply various stimuli on the GI tract of a subject, including mechanical and/or electrical stimuli, and/or induction of temperature alteration within the GI tract or any type of random combination of any of these stimuli. The improved gastrointestinal capsules or belts are further configured for dynamic alterations of the parameters of the stimuli during their operation in order to reduce/avoid habituation, thereby obtaining responsiveness for prolonged periods of time, to achieve, for example, effective long term weight loss, or long term proper GI motility. The present disclosure discloses for the first time the use of temperature alteration in a random way within the GI tract for the treatment of GI disorders and obesity.

As used herein, and throughout the application, the term "belt" may be replaceable with any wearable device.

According to one aspect, the present disclosure provides a gastrointestinal capsule or outside wearable belt configured to apply at least one physical stimulation selected from the group consisting of mechanical stimulation and electrical stimulation to a gastrointestinal tract wall (or a segment thereof) of a subject when activated inside the gastrointestinal tract of the subject. According to some embodiments, said capsule or belt comprises a controller configured to alter at least one parameter of said at least one physical stimulation during operation of the capsule inside the gastrointestinal tract of the subject. According to some embodiments, the controller is configured to dynamically alter at least one parameter of the stimuli. According to some embodiments, the controller is configured to randomly/pseudo-randomly alter at least one parameter of the stimuli. According to some embodiments, the controller is configured to randomly/pseudo-randomly alter a random combinations of several parameters of several types of stimuli.

As used herein, "configured to randomly alter at least one parameter", when referring to the controller, means that the controller is configured to alter parameter(s) of a stimulation between randomly or pseudo-randomly selected values. For example, the controller can be configured to alter the frequency of a vibration stimulation between a first frequency and a second frequency, wherein the second frequency is randomly selected by the controller according to an algorithm. In some embodiments, the first frequency is also randomly selected by the controller. Alternatively, or additionally, the term means that the controller is configured to alter parameter(s) of a stimulation at random time points during the operation of the capsule inside a gastrointestinal tract of a subject. For example, the controller can be configured to alter the frequency of a vibration stimulation between a first and second frequencies, e.g. about 0.1 to 60 minutes after activation of the capsule (after the beginning of stimulation application by the capsule), wherein the time is randomly selected by the controller. Similarly, the proprietary algorithm of the controller can also select any combination of different types of stimuli, and each of these types of stimuli by itself is being controlled randomly. Thus, according to some embodiments, the algorithm may provide random chaotic pattern of combination of stimuli for which the parameters of each of the types of stimuli is being randomly determined from the first beat to the following one. In some embodiments, the capsule or the belt are configured to apply a mechanical stimulation through vibration of the capsule or the belt, and the at least one parameter is vibration frequency.

Vibration frequency in the range of a few dozens of Hz corresponds to the normal frequency of peristaltic activity of the stomach and/or intestine. In some embodiments, the controller is configured to randomly alter the vibration frequency between values within the physiological range. In other embodiments, the controller is configured to randomly alter the vibration frequency between values below and above physiological values. In some embodiments, the controller is configured to randomly alter the vibration frequency between values ranging from about 0.01 to about 10,000 Hz or higher. In some embodiments, the controller is configured to randomly alter the vibration frequency between values ranging from about 0.01 to about 5,000 Hz, for example between about 0.1-1000 Hz. Each possibility represents a separate embodiment of the disclosure. In some embodiments, the controller is configured to randomly alter the vibration frequency between values ranging from about 1 to about 500 Hz. In some embodiments, the controller is configured to randomly alter the vibration frequency between values ranging from about 1 to about 50 Hz.

As used herein, the term "about", when referring to a measurable value, is meant to encompass variations of +/−10%, more preferably +1-5%, even more preferably +/−1%, and still more preferably +/−0.1% from the specified value, as such variations are appropriate to achieve the intended purpose.

In some embodiments, the capsule or the belt are configured to apply a mechanical stimulation through rotation of the capsule or the belt, and the at least one parameter is rotation frequency. In some embodiments, the controller is configured to randomly alter the rotation frequency between values ranging from about 10,000 cycles/second to 1 cycle/minute. In some embodiments, the controller is configured to randomly alter the rotation frequency between values higher than about 10,000 cycles/second and values lower than about 1 cycle/minute.

According to some embodiments, the capsule or the belt are configured to apply a mechanical stimulation through a mechanical movement of or within the capsule or the belt, for example through rotation or vibration of the capsule or of the belt. According to some embodiments, the pattern of the mechanical movement may be altered, for example vibration direction, rotation axis or others.

In some embodiments, the capsule or the belt are configured to apply a mechanical stimulation through an inflatable-deflatable balloon. In some embodiments, such capsule or the belt comprise a capsule or belt body comprising the controller, and a balloon functionally attached to said capsule body, said balloon is operative to inflate or deflate in response to a command from the controller, to thereby apply a mechanical stimulation to the gastrointestinal wall of a subject. According to these embodiments, the at least one parameter is a volume of the balloon, meaning that the volume of the balloon does not remain constant throughout the operation of the capsule or the belt. In some embodiments, the balloon is configured to be in contact with the gastric wall or intestinal wall (or portions thereof) upon its inflation. In some embodiments, the volume of the balloon is randomly altered between values ranging from about 10 ml to about 2000 ml, for example from about 300 ml to about 800 ml, for example between about 400-700 ml. Each possibility represents a separate embodiment of the present disclosure.

In some embodiments, the capsule is configured to apply a mechanical stimulation through vibration, rotation or a combination thereof, optionally through vibration, rotation, inflatable/deflatable balloon or a combination thereof.

In some embodiments, the capsule is configured to apply an electrical stimulation and the at least one parameter is selected from the group consisting of electric pulse frequency and electric pulse intensity or the combination thereof. Each possibility represents a separate embodiment of the disclosure.

The normal gastrointestinal myoelectric frequency is 3 cycles/minute (corresponds to 0.05 Hz). In some embodiments, the controller is configured to randomly alter the parameter(s) of the electrical stimulation between values within the physiological range. In other embodiments, the controller is configured to randomly alter the parameters(s) of the electrical stimulation between values below and above physiological values.

In some embodiments, the electric pulse frequency is altered between values ranging from about 0.01 to about 4000 Hz or even to about 10000 Hz. In other embodiments, the electric pulse frequency is altered between values in the range of about 0.00001-10000 Hz.

In some embodiments, the electric pulse intensity is altered between values ranging from about 0.01 to about 10000 mA, for example, from about 0.01 to about 500 mA.

In some embodiments, the frequency of the electric pulse is altered between values ranging from once every 0.0001 seconds to once every few hours.

In some embodiments, the capsule or the belt are further configured to generate a local temperature alteration in the immediate surroundings of the gastrointestinal capsule when the capsule is activated inside a gastrointestinal tract of a subject.

The capsule or the belt according to these embodiments may create a hypothermic effect or a hyperthermic effect. In some embodiments, the temperature ranges from about 4° C. to about 96° C. In some embodiments, the temperature alteration is induced for short periods of time, for example, several seconds or shorter.

According to another aspect, the present disclosure provides a gastrointestinal capsule or the belt configured to apply at least one physical stimulation selected from the group consisting of mechanical stimulation and electrical stimulation to a gastrointestinal tract wall (or a segment thereof) of a subject when activated inside the gastrointestinal tract of the subject, said capsule comprises a controller configured to alter at least one parameter of said at least one physical stimulation between above and below physiological values during operation of the capsule inside the gastrointestinal tract of the subject.

In some embodiments, the capsule is configured to apply a mechanical stimulation through vibration of the capsule, and the at least one parameter is vibration frequency.

In some embodiments, the controller is configured to alter the vibration frequency between values lower than about 10 Hz to values higher than about 100 Hz, for example, between values ranging between about 0.01-10 Hz to values ranging between about 100-10,000 Hz.

In some embodiments, the capsule is configured to apply an electrical stimulation and the at least one parameter is selected from the group consisting of electric pulse frequency and electric pulse intensity. According to some embodiments, electric stimulation may include electric-field stimulation, magnetic-field stimulation electromagnetic stimulation or any combination thereof. Each possibility represents a separate embodiment of the present disclosure.

In some embodiments, the controller is configured to alter the electric pulse frequency between values lower than about 0.05 Hz to values higher than about 1 Hz, for example, between values ranging between about 0.00001-0.05 Hz to values ranging between about 1-10,000 Hz.

In some embodiments, the controller is configured to alter the electric pulse frequency between values ranging from about 0.01 mA to about 10000 mA.

In some embodiments, the capsule or the belt are further configured to generate a local temperature alteration in the immediate surroundings of the gastrointestinal capsule when the capsule or the belt are activated inside a gastrointestinal tract of a subject. In some embodiments, the controller is configured to generate a local temperature alteration between values ranging from about 4° C. to about 96° C.

In some embodiments, the controller is configured to be pre-programmed to alter the at least one parameter or any type of combination of several parameters in a random chaotic way. In some embodiments, the controller is configured to be pre-programmed to alter the at least one parameter for each of the types of stimuli in a random chaotic way.

In other embodiments, the controller is configured to receive commands from an external source to alter the at least one parameter.

According to another aspect, the present disclosure provides a gastrointestinal capsule or belt configured to generate a local temperature alteration in the surroundings of the gastrointestinal capsule or belt when activated inside a gastrointestinal tract of a subject.

In some embodiments, the temperature ranges from about 4° C. to about 96° C. In some embodiments, the capsule or the belt are configured to induce the temperature alteration for short periods of time, for example about several seconds or less.

In some embodiments, the controller is configured to be pre-programmed to generate the local temperature alteration.

In other embodiments, the controller is configured to receive commands from an external source to generate the local temperature alteration.

In some embodiments, the controller is configured to be pre-programmed according to the subject physiological parameters including body weight, metabolic and cardiovascular status, and any other physiological parameter. The controller provides an algorithm which is based on these parameters and is thus patient-tailored.

In some embodiments, the controller is configured to receive data from the target organ, for example by sensing of biological indications.

In some embodiments, the controller is configured to have a learning machinery such that the stimuli generated are altered based on the data being received from different organs in the body.

In some embodiments, the capsule or the belt are further configured to apply at least one physical stimulation selected from the group consisting of mechanical stimulation and electrical stimulation to a gastrointestinal wall (or a segment thereof) of a subject.

In some embodiments, the capsules or the belts are of the present disclosure further comprise one or more arms configured to extend and anchor the capsules at a selected location within the GI tract.

In some embodiments, the position of the arms relative to the capsule body can be changed during the operation of the capsule between open and closed positions. In some typical embodiments, the extent to which the arms can be opened up ranges from 0% (arms closed, placed along the capsule body) to 100% (arms extend outwards, perpendicular to the capsule body). In some embodiments, the extent to which the arms are opened up is determined according to the diameter of a specific target area within the GI tract.

In some embodiments, operation or activation of the capsules disclosed herein is set to commence after a defined time-period following ingestion thereof, such that the capsule is activated as it reaches a target segment within the GI tract. The delay can range from a few seconds to a few hours. For example, for activation in the stomach, the capsule may be programmed to activate automatically within 1-10 seconds, or 15 minutes after ingestion.

According to yet another aspect, the present disclosure provides a stimulation device comprising an attachment element configured to be externally affixed to a subject's abdomen or any other area of the human body including the head, neck, arms, and legs, a stimulation module configured to apply a stimulation, e.g., mechanical and/or electrical stimulation, to at least a segment of the subject's abdomen or any other organ; and a controller configured to randomly alter at least one parameter, or any random combinations of parameters, of said mechanical and/or electrical stimulation during operation of the device. According to some embodiments, randomly altering the at least one parameter, or any random combinations of parameters, of mechanical and/or electrical stimulation comprises altering between above and below a physiological value. According to some embodiments, the attachment element is in the form of a belt, a strap, a sticker or any combination thereof.

According to yet another aspect, the present disclosure provides an external device configured to be affixed to a subject's abdomen or any other organ of the body, and apply at least one physical stimulation selected from the group consisting of mechanical stimulation and electrical or any other type of stimulation to a segment of the subject's body, said device comprises a controller configured to randomly alter at least one parameter of said at least one physical stimulation during operation of the device.

According to yet another aspect, the present disclosure provides an external device configured to be affixed to a subject's abdomen or any other organ, and apply at least one physical stimulation selected from the group consisting of mechanical stimulation and electrical stimulation, or any random combinations of these stimuli, to a segment of the subject's abdomen or any other organ, said device comprises a controller configured to alter at least one parameter of said at least one physical stimulation between above and below physiological values during operation of the device.

In some embodiments, the external device configured to be affixed to a subject's abdomen, or to any organ, is in the form of a belt.

In some embodiments, the devices disclosed herein are configured to induce a continuous stimulation. In other embodiments, the devices are configured to induce an intermittent stimulation. As used herein, "an intermittent stimulation" indicates a stimulation characterized by active periods ("on" periods) interleaved by pauses ("off" periods). According to these embodiments, the at least one altered parameter may comprise the "on" and "off" time periods. For mechanical stimulation applied by vibration and/or rotation, the "on" period is the period in which the capsule or the belt vibrates and/or rotates. When mechanical stimulation is applied through a balloon, the "on" period refers to the period in which the balloon is inflated. For electrical stimulation, the "on" period refers to the period in which electrical pulses are delivered.

The active period may range from a few parts of a second to a few dozens of minutes. The pauses may also range from a few parts of a second to a few dozens of minutes or hours.

In some embodiments, the controller is configured to be pre-programmed to randomly alter the at least one parameter.

In some embodiments, the controller is configured to be pre-programmed to randomly alter a combination of parameters for which each is being altered in a random chaotic way every part of a second to every few minutes or hours.

In other embodiments, the controller is configured to receive commands from an external source to alter at least one parameter to a random value.

In some embodiments, the devices described herein are configured to stimulate at least one part of the gastrointestinal tract selected from the group consisting of the mouth, esophagus, stomach, duodenum, small intestine, large intestine colon and rectum. Each possibility represents a separate embodiment of the disclosure.

In some embodiments, the devices described herein are configured to receive data from the target organs, by utilizing sensor(s) for obtaining measurements related to the activity of the target organ.

In some embodiments, the devices described herein are configured to change the algorithm based on the data being received from the target organ.

In some embodiments, the devices are used for the treatment of obesity or overweight.

In additional embodiments, the capsules or belts devices are used in the treatment of a gastrointestinal disease or disorder selected from the group consisting of gastroparesis, constipation, and intestinal pseudo-obstruction. Each possibility represents a separate embodiment of the disclosure.

In some embodiments, there is provided herein a method for treating a clinical condition selected from the group consisting of obesity and a GI motility disorder in a subject in need thereof, the method comprising introducing a gastrointestinal capsule as described herein into a gastrointestinal tract of the subject, and activating the gastrointestinal capsule.

In additional embodiments, a method is provided for treating a clinical condition selected from the group consisting of an inflammatory disease, an infectious disease, an autoimmune disease, a metabolic disease and a malignant disease, the method comprising introducing a gastrointestinal capsule into a gastrointestinal tract of a subject in need thereof, said capsule or belt are configured to apply at least one physical stimulation to a gastrointestinal tract wall when activated inside the gastrointestinal tract, the at least one physical stimulation is selected from the group consisting of mechanical stimulation, electrical stimulation and local temperature alteration; and activating said gastrointestinal capsule or belt.

In some embodiments, a method is provided for treating a clinical condition selected from the group consisting of an inflammatory disease, an infectious disease, an autoimmune disease, a metabolic disease, including for example diabetes type 1 and type 2, atherosclerosis, and any type of heart disease, and a malignant disease, the method comprising affixing an external device to a subject's abdomen, said external device is configured to apply at least one physical stimulation selected from the group consisting of mechanical stimulation and electrical stimulation to a segment of the subject's abdomen when affixed to said segment and activated; and activating said external device.

In some embodiments, the clinical condition is an inflammatory disease. In some embodiments, the inflammatory disease is an inflammatory bowel disease. In some embodiments, the inflammatory disease is a TNF-mediated inflammatory disease.

In some embodiments, the clinical condition is an infectious disease. The infectious diseases that can be treated include bacterial, viral, fungal and parasitic infections. Each possibility represents a separate embodiment of the disclosure. In some embodiments, the infectious disease is an infection of the gastrointestinal tract (chronic or acute). In other embodiments, the infectious disease is an infection outside the gastrointestinal tract. In some embodiments, the infectious disease is a systemic infection.

In some embodiments, the clinical condition is an autoimmune disease.

In some embodiments, the clinical condition is a metabolic disease. In some embodiments, the metabolic disease is diabetes.

In some embodiments, the clinical condition is a malignant disease. In some embodiments, the malignant disease is a malignancy of the gastrointestinal tract, such as malignancy of the gut. In some embodiments, the malignancy of the gut is selected from the group consisting of a precancerous condition, polyp, primary tumor and secondary tumor. Each possibility represents a separate embodiment of the present disclosure.

In other embodiments, the malignant disease is a malignancy outside the gastrointestinal tract, of body parts other than the gastrointestinal tract.

In some embodiments, the malignant disease is a malignancy of the gallbladder. In additional embodiments, the malignant disease is a malignancy of the pancreas.

In some embodiments, the capsule is configured to apply a mechanical stimulation through vibration, rotation or a combination thereof.

In some embodiments, the capsule or the belt are configured to apply a mechanical stimulation through vibration of the capsule. In some embodiments, the vibration frequency is the range of about 0.01 to about 10,000 Hz, for example between about 0.1-1000 Hz. In some embodiments, the vibration frequency is the range of about 10-100 Hz. In some embodiments, the capsule is configured to change the vibration frequency during its operation.

In some embodiments, the capsule or the belt are configured to apply a mechanical stimulation through rotation of the capsule. In some embodiments, the rotation frequency is in the range of about 10,000 cycles/second to about 1 cycle/minute. In some embodiments, the capsule is configured to change the rotation frequency during its operation.

In some embodiments, the capsule or the belt are configured to apply an electrical stimulation. In some embodiments, the electrical stimulation is characterized by a frequency in the range of about 0.01 to 4000 Hz, for example between about 0.01-1000 Hz. In some embodiments, the electrical stimulation is characterized by an intensity in the range of about 0.01 to 500 mA. In some embodiments, the capsule or the belt are configured to change the frequency and/or intensity of the electrical stimulation during its operation. Each possibility represents a separate embodiment of the disclosure.

In some embodiments, the capsule or the belt are configured to generate local temperature alterations in the immediate surroundings of the capsule within the GI tract. In some embodiments, the local temperature alterations are in the range of about 4° C. to about 96° C. In some embodiments, the temperature alterations are induced for short periods of time, for example, for several seconds or shorter.

In some embodiments, the capsule or the belt are configured to apply a continuous stimulation. In other embodiments, the capsule is configured to apply an intermittent stimulation.

In some embodiments, activation of the capsule or the belt are set to commence after a defined time-period following ingestion thereof, such that the capsule is activated as it reaches a target segment within the GI tract.

In some embodiments, the physical stimulation generated by the devices disclosed herein induce at least one physiological effect selected from the group consisting of decreased appetite, reduced absorption throughout the GI tract, increased GI motility, decreased GI motility, secretion of incretins and/or insulin, or any other type of a hormone, alteration of local or brain connected neuronal pathways and suppression of bacterial overgrowth. Each possibility represents a separate embodiment of the disclosure.

In some embodiments, there is provided herein a method for increasing GI motility in a subject in need thereof, the method comprising inserting and activating a gastrointestinal capsule as described herein to the GI tract of the subject.

In additional embodiments, there is provided herein a method for inducing malabsorption throughout the GI tract of a subject in need thereof, the method comprising inserting and activating a gastrointestinal capsule as described herein to the GI tract of the subject.

In additional embodiments, there is provided herein a method for treating bacterial overgrowth in the GI tract of a subject in need thereof, the method comprising inserting and activating a gastrointestinal capsule as described herein to the GI tract of the subject.

In some exemplary embodiments, the method is applied for the treatment of a *Clostridium difficile* infection. Without being bound by any particular theory or mechanism of action, it is contemplated that *Clostridium difficile* infection, whether chronic or acute, is inhibited by altering the motility of the gut directly or via the induction of hormones or any other type of mediators released locally or systemically.

In yet additional embodiments, there is provided herein a method for treating a disease or disorder associated with alteration of the gut microbiome in a subject in need thereof, the method comprising inserting and activating a gastrointestinal capsule or the belt are described herein to the GI tract of the subject.

In yet additional embodiments, there is provided herein a method for diagnosing a GI motility disorder in a subject, the method comprising inserting and activating a gastrointestinal capsule as described herein to the GI tract of the subject, and monitoring the motion of the gastrointestinal capsule within said GI tract of the subject.

Without being bound by any particular theory or mechanism of action, it is contemplated that beneficial effects generated by the devices described herein are induced, inter alia, by altering GI motility per se, and/or via induction of hormones and/or other mediators released locally or systemically. Thus, both local and systemic effects can be achieved. It is further contemplated that the stimuli generated by the devices described herein can affect the vagal nerve, and/or any type of sympathetic or parasympathetic innervations of the gastrointestinal tract, to thereby generate beneficial effects within the GI tract, as well as in other parts of the body. It is further contemplated that the stimuli generated by the devices described herein can affect the immune system, e.g., to alter chemokine and cytokine secretion from immune cells, to thereby generate beneficial effects within the GI tract, as well as in other parts of the body.

For each of the above type of signals delivered by the device, the random dynamics of the stimulation applied by the devices provides a way for overcoming the ability of the target organ or the brain, or the brain-gut axis, to accommodate to the delivered signal and thus preventing its effect. It also provides a way to prevent adaptation of the brain or any part of the gastrointestinal tract to the stimuli, thereby enabling a prolonged effect. According to some embodiments, the disclosed treatment methods and devices may be used for preventing weight regain following a weight-loss process, such as a diet or procedure or device used for weight reduction.

The randomization of the stimuli may include randomization of both the rate and magnitude of the stimuli.

These and further aspects and features of the present disclosure will become apparent from the figures, detailed description and claims which follow.

DETAILED DESCRIPTION

Figure 1:
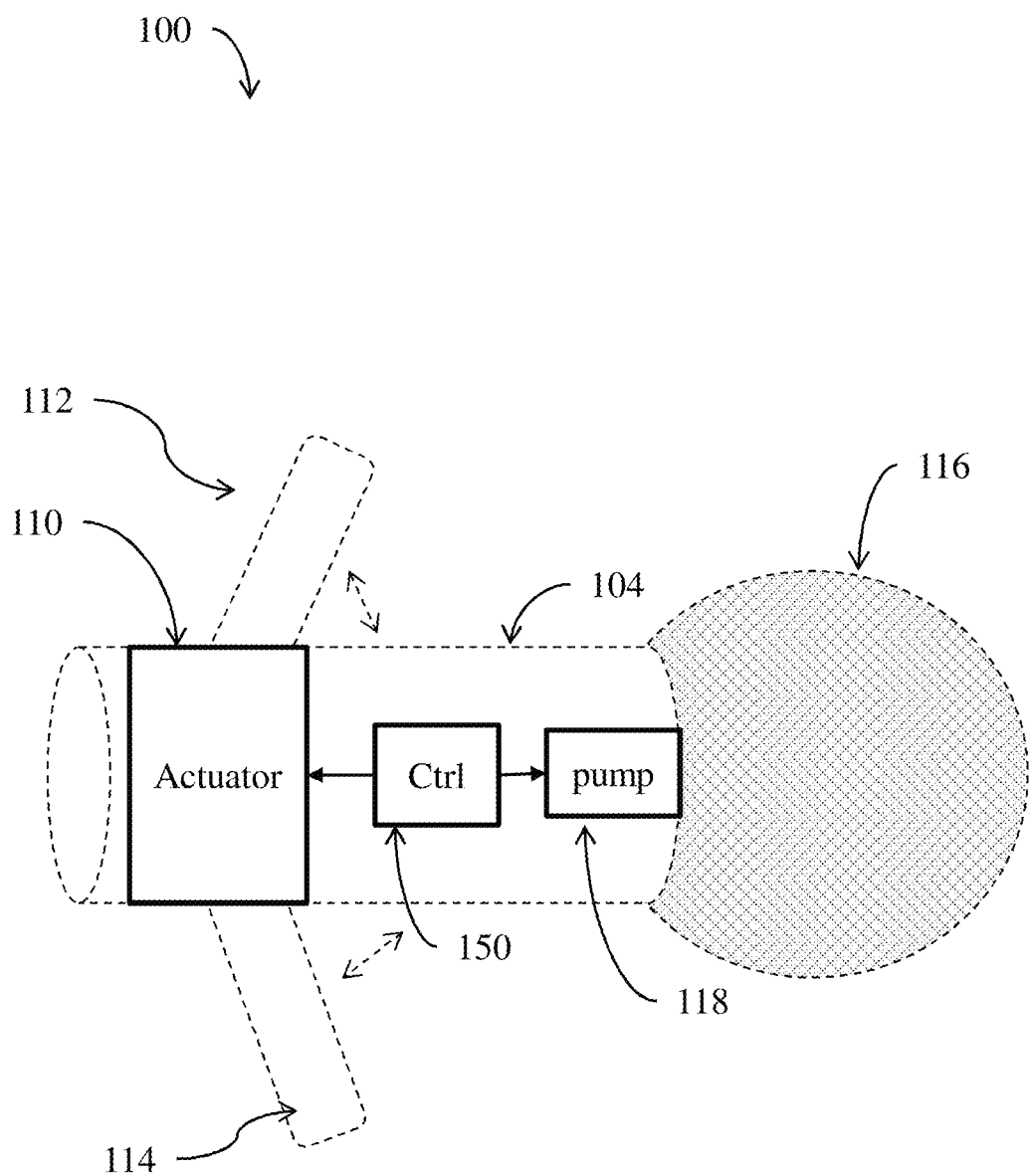
FIG. 1 schematically illustrates a stimulation capsule according to some embodiments.

Most organs in the human body function in a regular constant rhythm. Providing a regular stimuli to human organs is associated with adaptation of the organ within a certain period of time. A similar mechanism is leading to weight regain following dietary procedures.

Both—diets and endoscopic and surgical procedures, fail to maintain long term weight loss. Sustained weight loss and prevention of weight regain are therefore major problems. Most dietary procedures are effective only for short term.

Dieting is defined as an intentional effort to create a negative energy balance for the purpose of losing weight, at least in part through the restriction of energy intake. Dieting via a metabolic route (attempts to control weight using pills)—loss of lean tissue and reduced metabolic rate per kilogram of lean body mass. Biologically, the human body experiences the dieting process as a form of starvation. Therefore, the body shifts into primal survival mode, where the metabolism slows down and food cravings escalate. With each diet, the body learns and adapts, resulting in rebound weight gain. Dieting through a behavioral route (controlled eating habits)—increased hunger and reward value of food. This method disconnects the innate hunger and satiety cues, and it becomes easier to eat in the absence of hunger and develop a mistrust of the biological eating cues. Very-low-energy diets (VLEDs) which provides 800 kcal a day with high levels of protein and minimal carbohydrate to encourage weight loss with minimal loss of lean tissue, supplemented with vitamins, minerals, electrolytes and fatty acids to ensure adequate nutrition are used. However, all are associated with body adaptation and weight regain in a large proportion of the patients. For many dietary procedures, 90% of all dieters' regained weight over the course of 3 years. Endoscopic or surgical procedures to reduce the size of the stomach, intragastric balloon, to fill the stomach, and bariatric surgeries, such as—sleeve gastrectomy, biliopancreatic diversion, gastric bypass surgery, while achieving weight loss, are not successful for long-term weight management.

Appetite regulation involves a number of orexigenic and anorexigenic peptide hormones. Ghrelin-producing cells are identified throughout the gastrointestinal tract but enteroendocrine cells of the gastric fundus are the main source of its production. Ghrelin is the only circulating gut orexigenic hormone. It regulates energy metabolism and act as a signal of hunger. Ghrelin administration increases energy intake and induces weight gain. In the acute setting, its levels are elevated by fasting and suppressed following a meal or after an oral glucose tolerance test. At the chronic state, its levels increase in obese and are low in lean subjects. Ghrelin levels are enhanced under physiological stress. The ghrelin axis plays a role in energy homeostasis, adipogenesis, insulin regulation, reward associated with food stress-induced food intake.

Ghrelin is a dynamically regulated peripheral hunger signal. The vagal afferent pathway is the neural path by which information about ingested nutrients reaches the central nervous system (CNS) to influence feeding behavior. Ghrelin signals gut nutrients to the CNS and up-regulates food intake while lowering energy expenditure. In the CNS, ghrelin acts on hypothalamus and limbic system, known areas of regulation of appetite and energy expenditure. Its effects in the hypothalamus are mediated by homeostatic pathways to signal hunger, increase food intake and adiposity, promoting weight gain. AMP-activated protein kinase (AMPK) in the hypothalamus modulates energy balance. Ghrelin exerts its effect through a network of neuroendocrine links, including the melanocortin and endocannabinoid systems. Hypothalamic nuclei, the hippocampus, the amygdala, the caudal brain stem, and midbrain dopaminergic neurons play roles in the orexigenic actions of ghrelin. The only known ghrelin receptor is the growth hormone secretagogue receptor (GHSR) located in several distinct regions of the CNS.

Ghrelin acts centrally and by affecting the GI tract, increasing skeletal muscle growth and lipolysis, decreasing protein breakdown, and body fat utilization. Ghrelin administration causes hyperglycemia in both rodents and in humans. It inhibits insulin release from the pancreas, increases hepatic glucose production, and prevents glucose disposal in muscle and adipose tissues, which leads to hyperglycemia and impaired glucose tolerance. Ghrelin stimulates neuropeptide Y (NPY) neurons, but not pro-opiomelanocortin neurons, to regulate food intake.

As ghrelin is the only peripheral hormone to transmit satiety signal, inhibiting its signaling is being evaluated as a target for anti-obesity therapies. Efficacy of ghrelin was tested in diseases involving anorexia, negative energy balance, systemic inflammation, and gastroparesis, cancer, cachexia, cardiovascular disorders, chronic heart failure, chronic renal failure, chemotherapy, arthritis, and inflammatory bowel disease. Ghrelin agonists have been developed for the treatment of hypomotility disorders and the peptidomimetic TZP-102 is in phase 2 clinical trials for diabetic gastroparesis.

Weight loss causes changes in appetite and energy expenditure that promote weight regain. It is unclear whether the increases in ghrelin during weight loss are associated with regain. If circulating ghrelin participates in the adaptive response to weight loss, its levels should change with dieting. Although dietary restriction often results in initial weight loss, majority of obese dieters fail to maintain their reduced weight. Diet-induced weight loss results in a compensatory increase of hunger, decreased ghrelin suppression that encourage weight regain. Compensatory metabolic changes that accompany weight loss, including increased ghrelin levels, contribute to weight regain and difficulty in long-term weight loss maintenance. A recent review showed changes in ghrelin, leptin, and insulin during intentional weight loss with a follow-up period to promote weight regain.

Twelve weeks of high-fat diet feeding causes ghrelin resistance in arcuate neuropeptide Y (NPY)/agouti-related protein (AgRP) neurons. Diet-induced obese ghrelin-knockout mice exhibit less weight regain after calorie-restricted weight loss compared with wild-type mice, further supporting the notion that ghrelin mediates rebound weight gain after calorie-restricted weight loss.

Ghrelin levels are increased by fasting in lean rodents and are elevated before meals in humans, suggesting an important role for ghrelin in meal initiation. However, in obese human, circulating ghrelin levels were found to be significantly reduced as compared to lean individuals. Obesity-induces central ghrelin resistance regulates behavior and impaired ghrelin secretion from the stomach. Weight loss restores ghrelin secretion and function. It was suggested that ghrelin resistance is a mechanism that keep a higher body weight set-point during times of food availability. Ghrelin secretion was reduced in obese mice but its diurnal regulation was lost. No change in ghrelin secretion upon fasting and refeeding was noted. The sensitivity to the orexigenic effects of exogenous ghrelin was reduced in obese mice when compared to lean mice fed a chow or a lean fat diet. The insensitivity of obese mice to ghrelin was improved upon weight loss.

In a one year randomized controlled trial greater weight loss, achieved through a reduced calorie diet or exercise, was associated with increased ghrelin levels in overweight or obese postmenopausal women. The change in total ghrelin was inversely associated with changes in leptin, insulin and insulin resistance, and positively associated with change in adiponectin. In a randomized clinical trial, with a 12-month follow-up period, obese Mexican-American women following interventions including diet, exercise, and orlistat, ghrelin levels increased at 6 months but returned to baseline at 12 months in the weight loss group. Baseline ghrelin concentrations were directly related to the degree of weight loss achieved after 12 months. The data suggested that ghrelin rises in response to weight loss as a counter-regulatory mechanism. In a study of 193 obese adult men and women who were randomized to a low carbohydrate breakfast or an isocaloric diet with high carbohydrate and protein breakfast, a high carbohydrate and protein breakfast prevented weight regain by reducing diet-induced compensatory changes in hunger, cravings and ghrelin suppression.

Population-based studies suggest that repetitive cycling of weight loss and regain may be associated with future weight gain. A cross-sectional study evaluated the relationship between a history of frequent weight loss and biomarkers, including serum ghrelin in one hundred fifty-nine weight stable overweight postmenopausal women. A higher degree of weight cycling, characterized by the frequency of intentionally losing more than 10 lb, was associated with an appetite-stimulating hormonal profile, including higher concentrations of ghrelin. In another study, of 88 overweight/obese patients who received an 8-week hypocaloric diet program and were categorized as regainers (>/=10% weight-lost regain) and non-regainers (<10% weight-lost regain) 6 months after finishing the dietary treatment, regainers showed a higher baseline and after treatment leptin/ghrelin ratio (L/G) than non-regainers. Subjects with higher plasma leptin and lower ghrelin levels at baseline were more prone to regain lost weight.

In a prospective study of 43 patients treated with BioEnterics intragastric balloon, ghrelin hyper-response in non morbid obese patients was characterized with greater short-term treatment efficiency and leaning to weight regain of obesity. In a five years follow up study after sleeve gastrectomy (SG), significant weight regain and severe reflux were described in some patients. Ghrelin levels remained low postoperatively. Ghrelin levels were reduced after gastrectomy and did not recover by 12 months postoperatively. In this trial, the appetite score increased significantly by 12 months. A diet-induced weight loss after gastric bypass of 17% of initial body weight was associated with a 24% increase in the area under the curve for the 24-hour ghrelin profile. Gastric bypass was associated with markedly suppressed ghrelin levels, contributing to the weight-reducing effect of the procedure.

Weight regain is a major concern following Roux-en-Y gastric bypass (RYGB). In a study of 24 patients, secretion of gut hormones in patients with weight regain after RYGB was different from that in patients with satisfactory weight outcome. After meal stimulation, reduced levels of GIP and GLP-1 may indicate the influence of gut hormones in the process of weight regain. There was no difference in the ghrelin secretion. In a follow up of 45 patients, higher preoperative ghrelin levels might identify patients that are more susceptible to weight regain after RYGB. In another study, measurement of ghrelin, insulin, and leptin before surgery is not useful as predictors of weight loss or regain at long term after RYGBP.

The SHAPE (Screened Health Assessment and Pacer Evaluation) trial was a 24 month randomized multicenter placebo-controlled study to determine the efficacy of an implantable gastric stimulator (IGS) for weight loss. At 24 months the control group exhibited weight gain from baseline that was significantly different from the weight loss in the treatment group. At 12 months, fasting ghrelin was significantly increased in the treatment group but not in the control. No significant change was observed in postprandial suppression of plasma ghrelin or in fasting and postprandial PYY levels. The data suggested that IGS does not prevent the increase in fasting plasma ghrelin levels associated with weight loss.

The present disclosure provides, in accordance with some embodiments, devices for stimulating a target organ, such as the gastrointestinal tract or any other organ in the human body. In some embodiments, a gastrointestinal capsule is provided, capable of applying a physical stimulation to the walls of different parts of the GI tract.

In other embodiments, an external device is provided, such as a belt configured to be worn by a subject, and when worn, to apply a physical stimulation to a target organ, such as a portion of the GI tract.

According to some embodiments, the devices disclosed herein are characterized by chaotic dynamics (chaotic rhythm) of the stimulation, meaning that they are configured to randomly alter the parameters of the stimulation during their operation. According to some embodiments, the terms "chaotic" and "random"/"randomly" can be used interchangeably. According to some embodiments, the chaotic/random type of the stimuli may be induced by different patterns, different magnitude or different rhythms of the stimuli, each of them by itself, or all together. According to some embodiments, the devices disclosed herein are characterized by chaotic dynamics (chaotic rhythm) of the stimulation, meaning that they may be configured to randomly select different combinations of various types of stimuli each being altered in a random way. According to some embodiments, the chaotic/random type of combination of stimuli may be induced by different patterns, different magnitude or different rhythms of the stimuli, each of them by itself, or all together.

As used herein, a "gastrointestinal capsule" refers to a capsule that propels and operates in the gastrointestinal tract. As used herein, the term "gastrointestinal" refers to the mouth, esophagus, stomach, duodenum, small intestine, large intestine and colon and rectum. The gastrointestinal capsule applies direct stimulation to different parts of the gastrointestinal tract. It is to be understood though that the effects resulting from the direct, local stimulation are not limited to the gastrointestinal tract or the digestive system. Systemic effects may result, affecting body parts within and outside the digestive system.

As used herein, the term "belt" refers to any type of external device that can deliver the stimuli. These include any type of wearable devices, such as neck chain, a watch, a patch that can be put anywhere on the skin, a rectal device, a bracelet, any type of an undershirt of underwear, any type of a shirt, pants, or socks, or shoes, heats, or any other wearable device.

As used herein, and throughout the disclosure, the terms "random", "pseudo-random" and "dynamic" and "chaotic" may be interchangeable, and refer to changes, in the stimuli parameter(s), that are arbitrary or unsystematic, at least to the extent of preventing or reducing a habituation effect for the stimuli in the target organ/region.

According to some embodiments, the changes, being random/pseudo-random, may apply to parts of the stimuli and not necessarily to others. For example, the stimuli signal may include multiple frequencies, and the random/pseudo-random changes may be applied to some of the frequencies, and not apply to the other frequencies.

According to some embodiments, the stimuli may include different sections/intervals being applied at different times. According to some embodiments, the stimuli parameter(s) in some sections/intervals may be changed/altered randomly, while not so in other section/intervals.

For example, in some embodiments, the capsule or the belt of the present disclosure induces indirect effects on organs associated directly or indirectly with the GI tract, including, for example, the gallbladder, liver, and pancreas, meaning that the capsule is not operated within these organs but may induce systemic effects affecting these organs. These devices can also exert an effect on other organs in the body which are not part of the gastrointestinal tract.

The devices according to some embodiments of the present disclosure includes means for optimized control over parameters such as the length, intensity and frequency of the stimulation, as well as novel means to induce the stimulation comprising temperature alteration. The devices may operate at low and/or high frequencies, that can be selected and varied according to specific needs. The devices according to some embodiments of the present disclosure generate local physical stimulation that may affect various processes regulated in the digestive system or any other organ system in the body. It is contemplated that the local physical stimulation activates reflex arcs and regulation pathways involving the digestive system. The present disclosure further provides methods and uses of such devices in various clinical and diagnostic applications.

The Gastrointestinal Stimulation Capsule

The capsule according to embodiments of the present disclosure is preferably swallowable and ingested by a subject in need. After ingestion, the capsule is propelled through the GI tract by the normal peristaltic motion of the GI tract, and. expelled naturally.

Alternatively, the capsule may be arranged to be inserted into the GI tract using an invasive procedure, an endoscopic procedure, a laparoscopic surgery procedure and/or a surgical laparotomy procedure.

The capsule is configured to induce a mechanical stimulation, electrical stimulation, temperature/thermal alteration, or a combination thereof.

In some embodiments, the mechanical stimulation is applied by the capsule through vibration, rotation or a combination thereof. Mechanical vibrations and/or rotations may be excited in the chyme contained within a segment of the GI tract and/or directly applied to the walls of the GI tract by the vibrating/rotating capsule. Thus, direct contact of the capsule with the GI tract inner surface may not be required in order to induce mechanical stimulation. Movement of the capsule to induce a mechanical stimulation is accomplished by elements embedded in the capsule, as is known in the art.

The elements that constitute the capsule are typically biocompatible and a-traumatic. They may comprise any suitable material, such as metal or plastic, or a combination thereof.

The capsule according to embodiments of the present disclosure typically comprises a power source, such as a battery, to provide power to all electrical elements of the capsule. According to some embodiments, the power source may be rechargeable and/or replaceable.

The capsule may be rounded or oval. Typically, the diameter of the capsule body ranges from about 8-15 mm. Typical length of the capsule body ranges from about 10-20 mm. If arms are included, their length is typically up to about 50 mm.

Reference is now made to FIG. 1, which shows a schematic illustration of a capsule according to some embodiments of the present disclosure. The capsule 100 comprises a capsule body 104 capable of inducing a mechanical stimulation and/or an electrical stimulation and/or temperature/thermal alteration, utilizing a stimuli delivery mechanism such as one or more arms 112 and 114, and a controller, such as control circuitry 150 for instructing the operation of an actuator 110 to move one or more of arms 112 or 114 relative to capsule body 104. According to some embodiments, the position of arms 112 or 114 relatively to capsule body 104 can be controlled and changed from open to closed and vice versa. According to some embodiments, capsule 100 further comprises an inflatable/deflatable balloon 116 functionally and mechanically connected to capsule body 104, wherein the inflating/deflating thereof is controlled via a pump 118 that is configured to pump gas and/or fluid in and from balloon 116. According to some embodiments, pump 118 and balloon 116 may be connected to a gas container within capsule body 104 for providing gas to and from balloon 116.

The External Device

The external device according to embodiments of the present disclosure is preferably affixed onto the subject's body. In some embodiments, the external device is in the form of a belt configured to be worn by a subject around the subject's waists or torso. In some embodiments, the external device is in the form of a patch or a watch or a bracelet or any type of a wearable object including hats, socks, shoes. Following attachment, the external device is operated to induce at least one physical stimulation, such as a mechanical stimulation. In some embodiments, the mechanical stimulation is applied through vibration, induction of pressure or other mechanical stimulations. In some embodiments, the stimulation is applied through change in temperature, or any other type of physiological signal that can be generated by the device, including light, or any other type of energy transfer.

Figure 2:
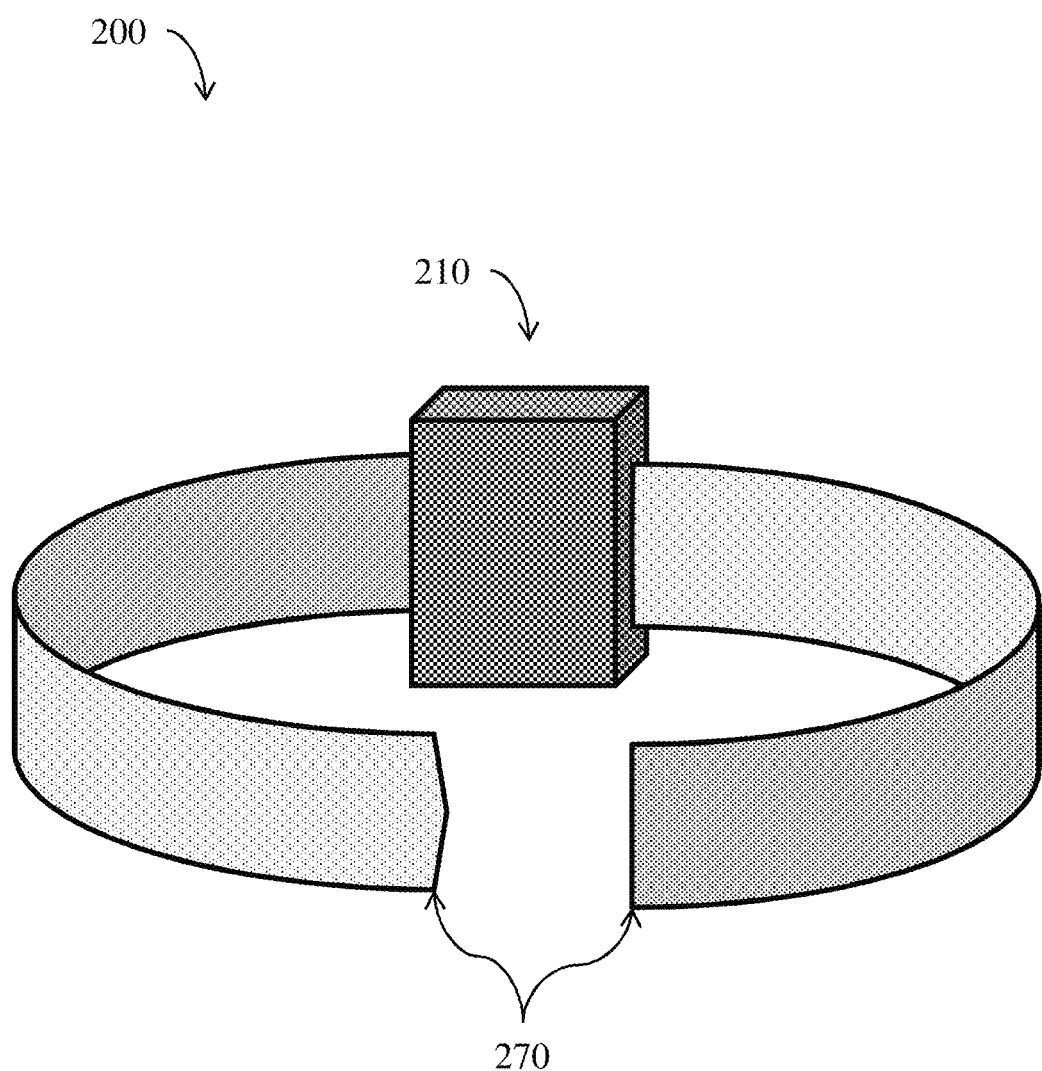
FIG. 2 schematically illustrates an external stimulation device, according to some embodiments.

Reference is now made to FIG. 2 which shows a schematic illustration of an external device 200 according to some embodiments of the present disclosure in the form of a belt configured to be affixed around a subject's waists or torso. Device 200 further comprises a stimulation unit 210 capable of inducing a mechanical stimulation. Stimulation unit 210 comprises an internal controller (not shown) configured to control the parameters of the stimulation. Device 200 further comprises means for affixing thereof to the body of the subject such as strap 270.

According to some embodiments, the controller can be integrated within the device (capsule or wearable), or alternatively, the controller may include an external processing circuitry with communication with the stimulation providing unit(s). such a controller may include a mobile device such as a cellphone or a tablet, a desktop, a laptop, a server or the like. According to some embodiments, the external controller may be in communication with the gastrointestinal capsule or the belt.

Figure 3:
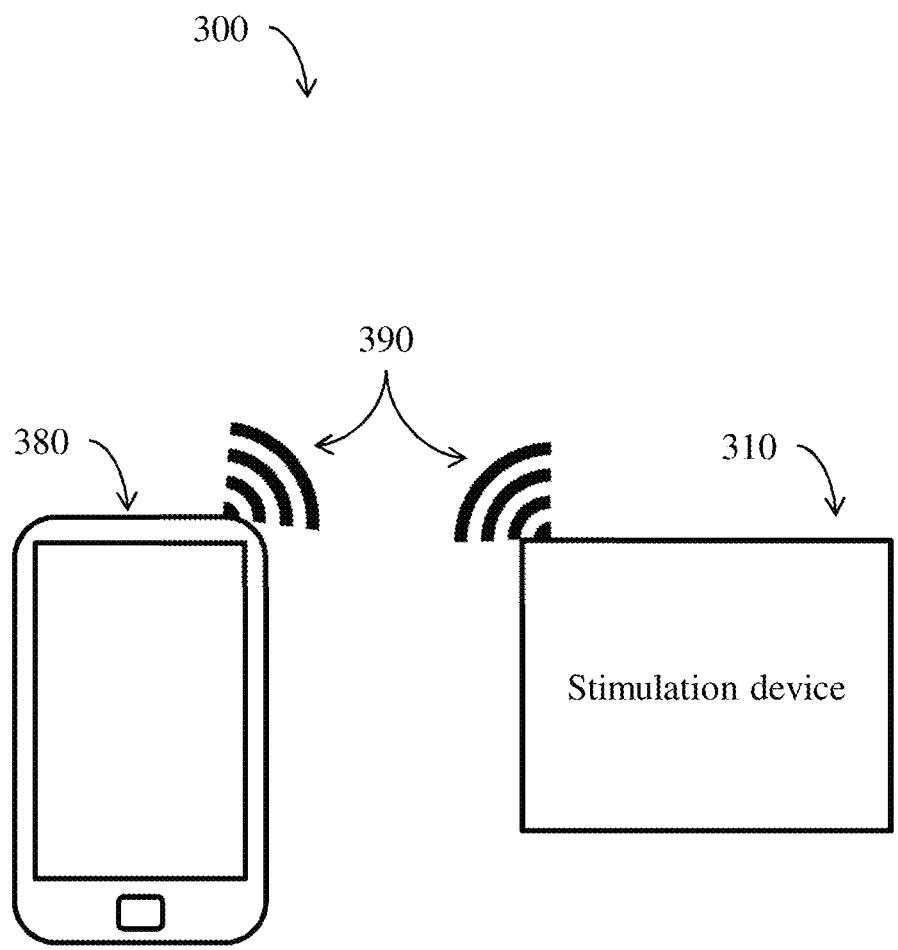
FIG. 3 schematically illustrates a setting of an external controller and a stimulation device, according to some embodiments.

Reference is now made for FIG. 3, which schematically illustrates a setting 300 of an external controller, such as a mobile device 380, and a stimulation device 310, according to some embodiments. According to some embodiments, mobile device 380 is configured to be in communication with stimulation device 310 via wireless communication link 390. According to some embodiments, wireless communication link 390 may be Wi-Fi, Bluetooth, IR, NFC, or the like.

According to some embodiments, the randomization/alteration technique/algorithm may be configurable based on user characteristics and/or previous learnings. According to some embodiments, the technique(s) may be based on the metabolic rate of the user, age, health state of others.

According to some embodiments the controller will have an embedded algorithm that will generate the random combination of stimuli.

According to some embodiments the controller is also a receiver of data generated in the target organ.

According to some embodiments the controller has a self-learning algorithm that can change the type of stimuli it delivers based on the data it receives from the target organs.

According to some embodiments these changes can be made instantly thus that the immediately followed stimuli is already changed according to the internal learning machinery.

Induction of Stimuli to Other Organs

In some embodiments, stimulatory devices characterized by chaotic dynamics of stimulation may be used to induce stimuli to organs other than the GI tract.

In some embodiments, the stimulatory devices are configured to be inserted into the target organ using an invasive procedure, including an endoscopic procedure, a radiological procedure or a surgical procedure, including a laparoscopic surgical procedure.

In some embodiments, the stimulatory devices may induce at least one physical stimulation selected from the group consisting of mechanical stimulation, electrical stimulation and temperature alteration. Each possibility represents a separate embodiment of the present disclosure.

Figure 4A:
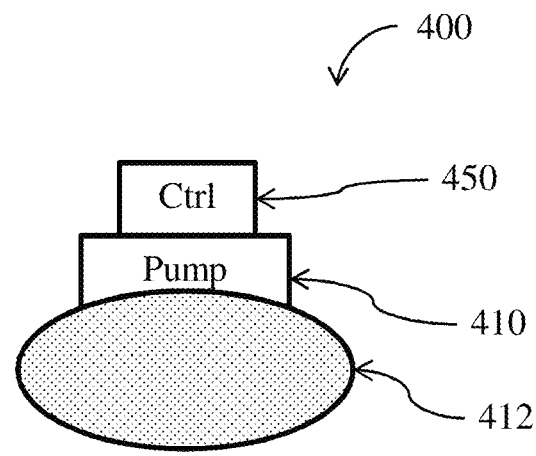
FIG. 4a schematically illustrates a stimulation capsule with a balloon at a first state, according to some embodiments.

Reference is now made to FIG. 4a, which schematically illustrates a stimulation capsule 400 with a balloon 412 at a first state, according to some embodiments. According to some embodiments, stimulation capsule 400 is configured to provide stimuli by means of applying pressure and/or filling of a volume space, by means of inflating and deflating of a balloon 412. According to some embodiments, the inflation and deflation is performed utilizing a pump 410 controlled by a control circuitry 450, which is configured to apply a stimulation pattern by means of inflation and deflation in a dynamic randomized/nonsystematic manner. As illustrated, balloon 412 is in a deflated state.

Figure 4B:
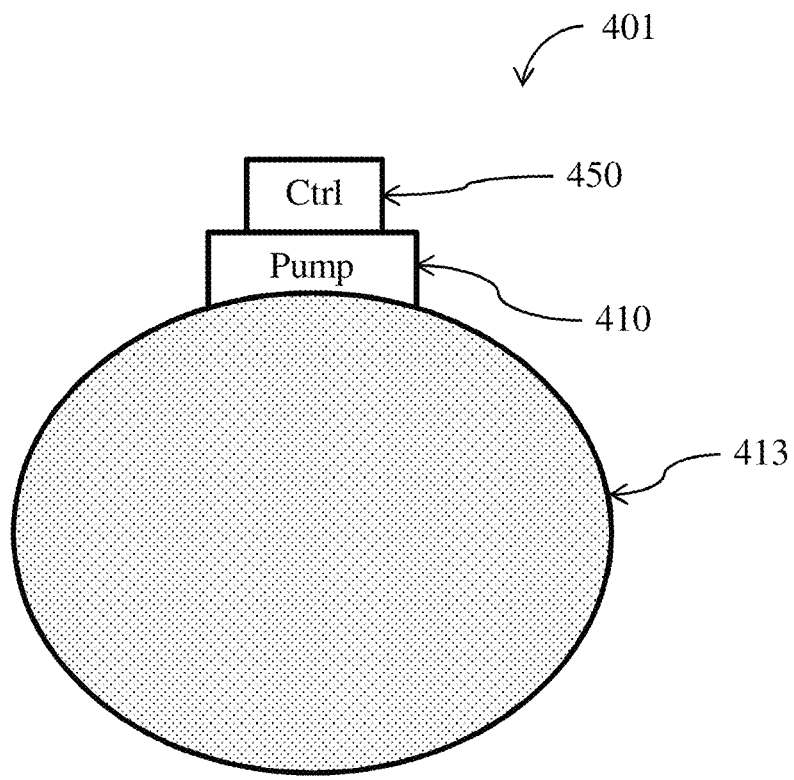
FIG. 4b schematically illustrates a stimulation capsule with a balloon at a second state, according to some embodiments.

Reference is now made to FIG. 4b, which schematically illustrates a stimulation capsule 401, essentially as disclosed in FIG. 4a stimulation capsule 400, with a balloon 413 at a second state, according to some embodiments. As illustrated, balloon 413 is in an inflated state, wherein pressure may be applied to a surrounding tissue of stimulation capsule 401.

According to some embodiments, the capsule or the external devices may be configured to apply/deliver stimuli by means of physical movement thereof. For example, the physical movement may include vibration, rotation of the like.

Figure 5:
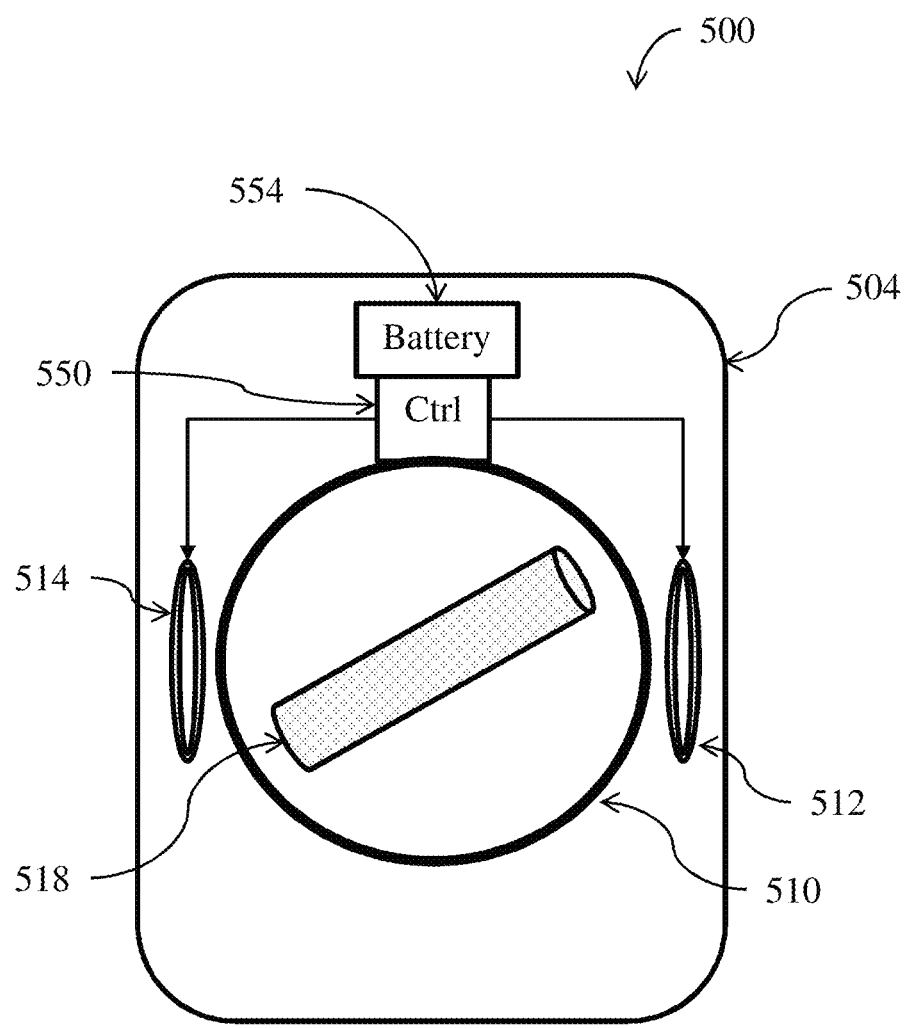
FIG. 5 schematically illustrates a magnetically actuated vibrating stimulation capsule, according to some embodiments.

Reference is now made to FIG. 5, which schematically illustrates a magnetically actuated vibrating stimulation capsule 500, according to some embodiments. According to some embodiments, stimulation capsule 500 is configured to provide stimulation by vibration, achieved via movement of a magnetic element, for example a magnetic elongated element/member, such as a magnetic shaft 518 in an enclosure 510 within capsule body 504, thereby affecting a movement of capsule body 504 at a controlled pace.

According to some embodiments, the movement of magnetic shaft 518 may be achieved by changes in the magnetic field surrounding it, for example by activation of magnetic field modifying elements, such as electromagnets 514 and 512, which are controlled by a controller 550 applying an altering operation signal. According to some embodiments, capsule 500 and components therein may be operated by electric power supplied via a battery 554 within capsule body 504.

According to some embodiments, other mechanisms may be utilized for achieving physical movement of the capsule, for example, an actuator (electric motor) configured to mechanically rotate an elongated shaft. According to some embodiments, the rotation of the elongated shaft may be done on a rotation axis that does not pass through the center of mass of the elongated shaft.

Figure 6:
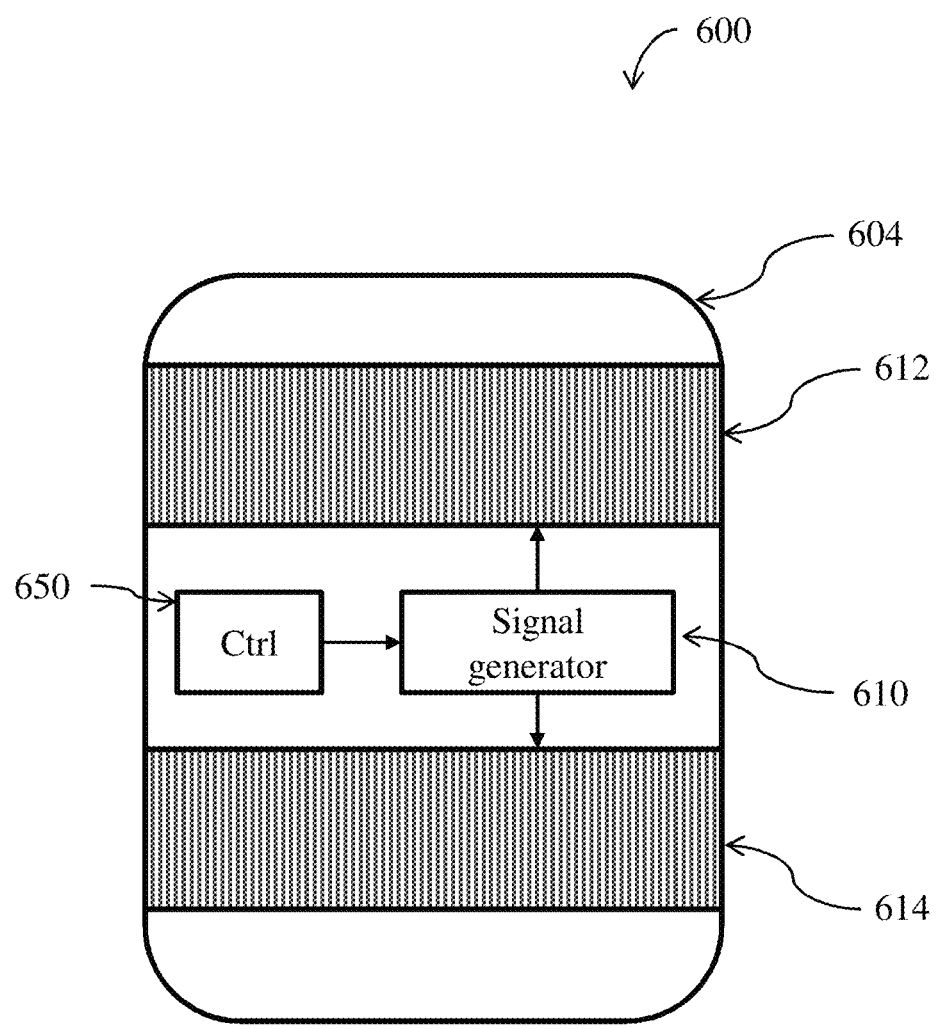
FIG. 6 schematically illustrates a stimulation capsule with electrodes, according to some embodiments.

Reference is now made to FIG. 6, which schematically illustrates a stimulation capsule 600 with electrodes, such as a first electrode 612 and a second electrode 614, according to some embodiments. According to some embodiments, first electrode 612 and second electrode 614 are assembled on a capsule body/housing 604 or integrally formed therewith, being at least partially exposed for having electric contact with the environment of stimulation capsule 600. According to some embodiments, first electrode 612 and second electrode 614 are provided with a stimulation signal by a signal generator 610 which is configured to produce a stimulation signal based on parameter configurations received from a controller, such as processing circuitry 650. According to some embodiments, processing circuitry 650 is configured to alter the parameters to generate a semi-random or non-systematic stimuli, for preventing habituation.

Figure 7:
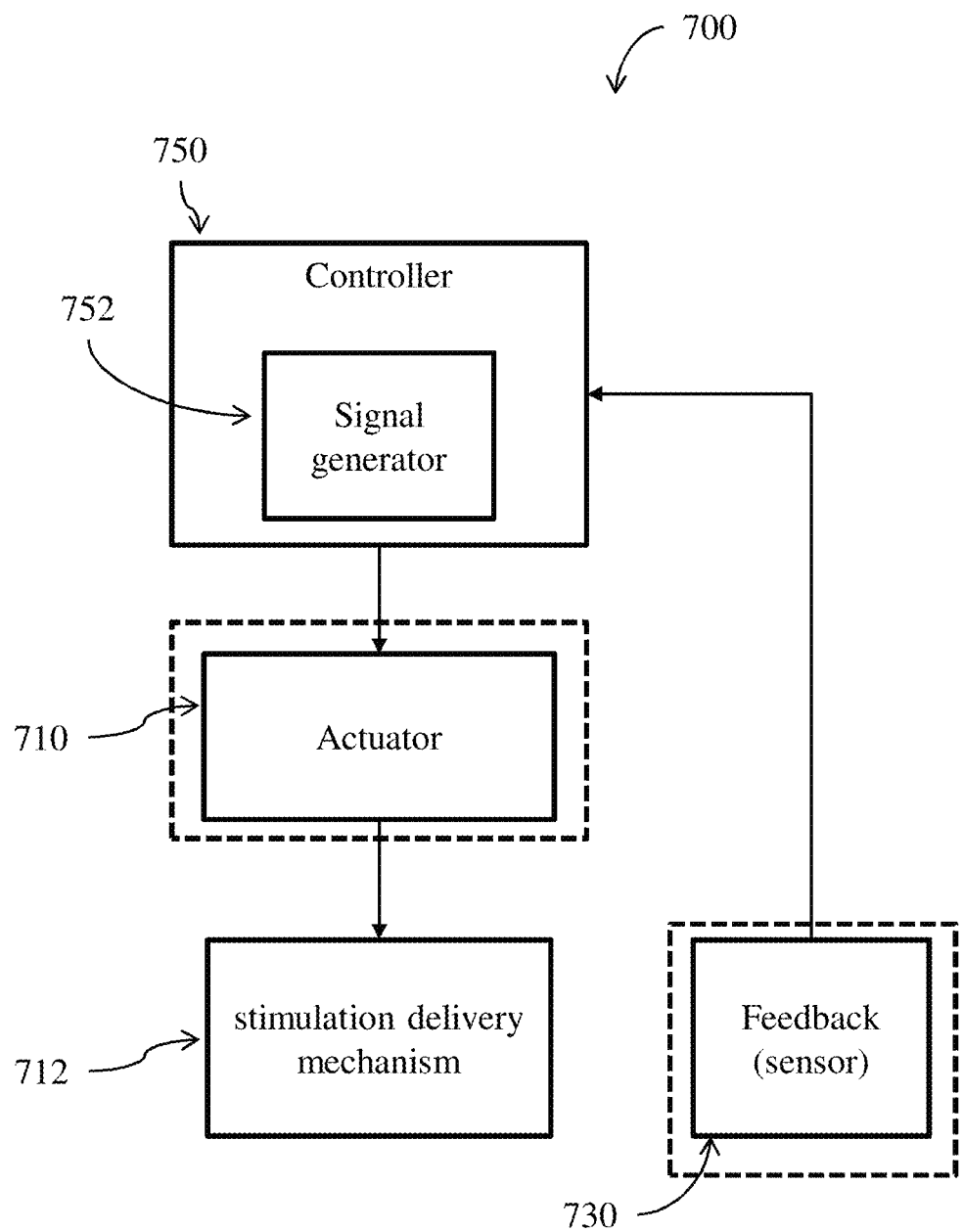
FIG. 7 illustrates a block diagram of a stimulation device, according to some embodiments.

Reference is now made to FIG. 7, which illustrates a block diagram of a stimulation device 700, according to some embodiments. In general, according to some embodiments, stimulation device 700 may include a controller 750 that may have imbedded therein a signal generator 752 for producing a randomly altering signal to be delivered to an actuator (optional) 710 which is configured to operate a stimulation delivery mechanism 712. Optionally, according to some embodiments, stimulation device 700 may include a sensor 730 for obtaining measurements indicative of the effect of the stimuli. According to some embodiments, sensor 730 may include a temperature sensor, or a detector configured to detect certain molecules, and the measurements may then be sent back to controller 750 for changing the stimulation parameters based thereon. According to some embodiments the controller also includes a receiver configured to receive data from the target organs, for example by means of measuring parameters indicative of an operation or state of the organ. According to some embodiments, the embedded algorithm may have an internal learning machinery which can alter the generated stimuli based on the data being received/measured from the organ by the controller.

According to some embodiments the controller can generate a feedback loop based on the data it receives.

In some embodiments the gastrointestinal capsule or external device are configured to induce a stimulation which is based on pre-programmed patient's tailored algorithm which is based on body weight, BMI, metabolic, endocrine, and other physiologic parameters of the subject.

Figure 8:
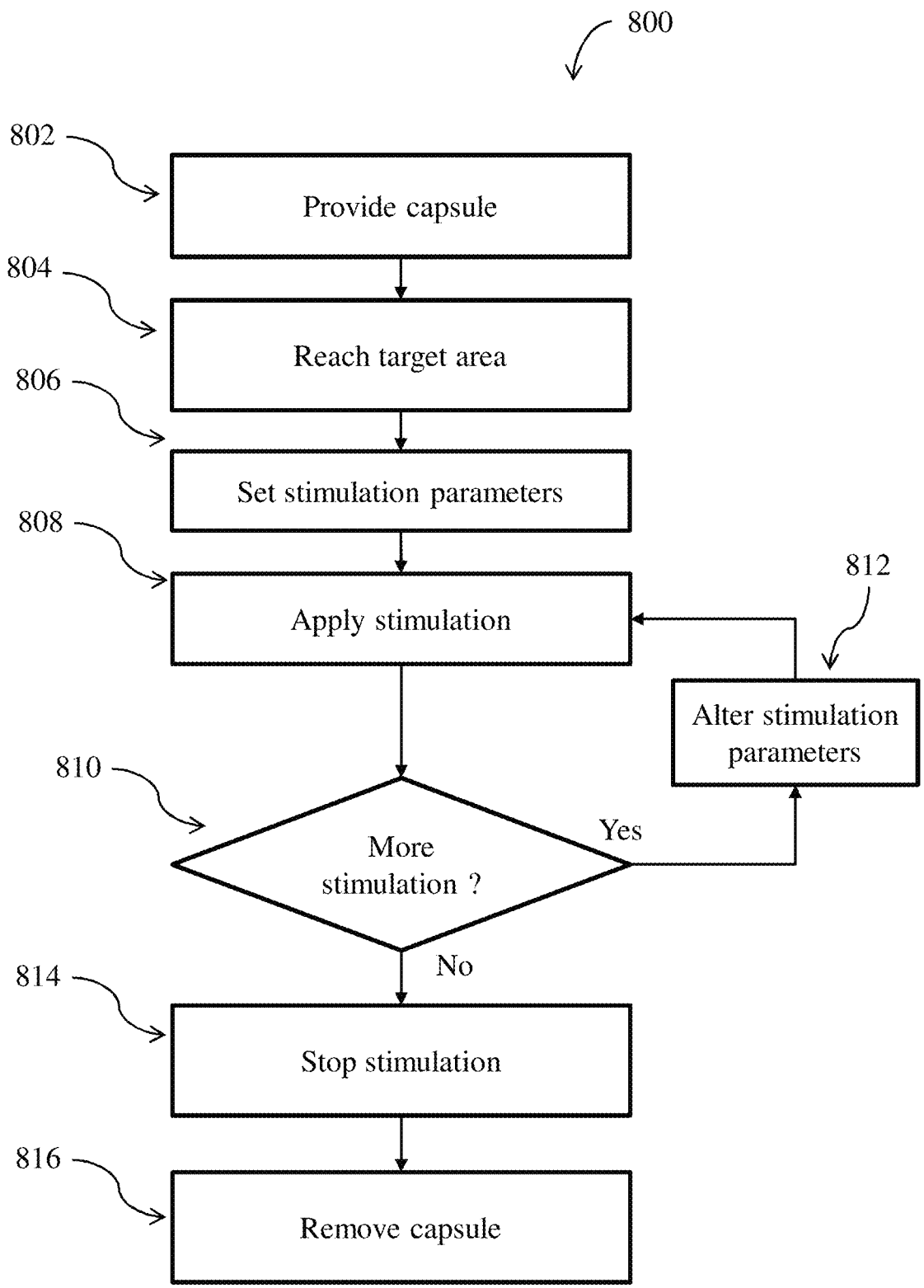
FIG. 8 illustrates a flow chart of a stimulation method, according to some embodiments.

Reference is now made to FIG. 8, which illustrates a flow chart of a stimulation method 800, according to some embodiments. According to some embodiments, Method 800 begins with providing a stimulation capsule to a user (step 802), then directing the capsule to a target organ or region (step 804), then stimulation parameters are set (step 806) and stimulation is delivered to the target region (step 808). According to some embodiments, if further stimulation is needed (step 810), the stimulation parameters may be altered (step 812), and stimulation may be applied based on the recently altered parameters (step 808) for mitigating or eliminating a habituation effect. Otherwise, stimulation may be terminated (step 814) and the capsule may be removed (step 816).

Therapeutic Utility

Without being bound by any particular theory or mechanism of action, it is contemplated that the local stimulation applied by the devices disclosed herein induces a systemic effect. For example, it is contemplated that the local stimulation induced by a gastrointestinal capsule or an external stimulatory device as disclosed herein induces the release of small peptides, hormones, cytokines and/or other molecules from the GI tract wall. In addition, the stimulation may induce release of such molecules from cells associated with the immune system in the gut. Thus, a stimulation applied by the capsule may result in both local and systemic effects. The stimulation may alter the function (inhibit or activate) of the nervous system of the gut. This can be achieved via altering the vagus and/or other parts of the sympathetic or parasympathetic nervous system of the gut.

Molecules released in the gut, in response to the stimulation may reach the brain and lead to various effect including appetite suppression. The secreted molecules may also work on various parts of the gut wall itself and lead to decreased absorption. The secreted molecules may also work on various parts of the gut wall itself to alter their motility either suppressing or enhancing motility. The secreted molecules may also work on various parts of the brain to secrete further molecules or to activate neuronal pathways that will alter the gut motility, either enhancing, or decreasing, or altering appetite. In addition, the stimulation mediated by the devices disclosed herein may affect regulation pathways controlling the GI motility. Increased motility can be therefore achieved as a result of direct contact of the capsule with the GI tract wall, as well as a result of systemic effects. Increased motility mediated by the devices according to the present disclosure is not limited to the area which is in close proximity to the capsule.

The devices according to embodiments of the present disclosure may be useful in the treatment of various clinical conditions associated with the digestive system, for example, obesity and/or GI motility disorders.

According to an aspect of the present disclosure, there is provided herein a method for treating obesity in a subject in need thereof, the method comprising inserting and activating a gastrointestinal capsule according to embodiments of the present disclosure to the GI tract of the subject.

According to another aspect, the present disclosure provides a method for treating 30 GI motility disorders in a subject in need thereof, the method comprising inserting and activating a gastrointestinal capsule according to embodiments of the present disclosure to the GI tract of the subject.

Non-limiting examples of GI motility disorders include diarrhea, constipation, ileus and gastro-paresis.

According to yet another aspect, the present disclosure provides a method for increasing GI motility in a subject in need thereof, the method comprising inserting and activating a gastrointestinal capsule according to embodiments of the present disclosure to the GI tract of the subject.

An increase in GI motility induced by the capsule according to embodiments of the present disclosure, in particular an increased small bowel movement, may induce malabsorption due to increase or decrease in the transition time.

According to yet another aspect, the present disclosure provides a method for inducing malabsorption throughout the GI tract of a subject in need thereof, the method comprising inserting and activating a gastrointestinal capsule according to embodiments of the present disclosure to the GI tract of the subject.

An increase in GI motility induced by the capsule according to embodiments of the present disclosure, in particular an increased small bowel movement, may assist in cases of bacterial overgrowth. This may be achieved by altering the motility of the gut via the induction of hormones or any other type of mediators released locally or systemically or by altering neuronal pathways either local or connected to the brain.

According to another aspect, the present disclosure provides a method for treating bacterial overgrowth in the GI tract of a subject in need thereof, the method comprising inserting and activating a gastrointestinal capsule according to embodiments of the present disclosure to the GI tract of the subject.

According to another aspect, the present disclosure provides a method for treating an infection in the gastrointestinal tract of a subject in need thereof, the method comprising inserting and activating a gastrointestinal capsule according to embodiments of the present disclosure to the gastrointestinal tract of the subject.

According to another aspect, the present disclosure provides a method for treating an inflammatory disease, including an inflammatory bowel disease, in the gastrointestinal tract of a subject in need thereof, the method comprising inserting and activating a gastrointestinal capsule according to embodiments of the present disclosure to the gastrointestinal tract of the subject.

According to another aspect, the present disclosure provides a method for treating a disease of the gallbladder, the pancreas, or other organ directly or indirectly associated with the gastrointestinal tract in a subject in need thereof, the method comprising inserting and activating a gastrointestinal capsule according to embodiments of the present disclosure to the gastrointestinal tract of the subject.

According to another aspect, the present disclosure provides a method for treating a cancerous condition, including a precancerous condition, polyp, primary or secondary tumor and metastases, in the gastrointestinal tract of a subject in need thereof, the method comprising inserting and activating a gastrointestinal capsule according to embodiments of the present disclosure to the gastrointestinal tract of the subject.

In some embodiments, the methods described herein are applied for the treatment of a disease selected from the group consisting of pancreatic cancer, acute or chronic pancreatitis, a premalignant polyp, Barrett's esophagus, a primary or secondary tumor of any part of the GI tract. Each possibility represents a separate embodiment of the present disclosure.

The methods described herein may also be applied for the treatment of diseases that are associated or augmented by bacterial translocation or alteration of the gut microbiome and/or gut flora derangement, diseases in which the immune system plays a role, including but not limited to chronic liver diseases and Alzheimer disease, hepatic encephalopathy, ADHD, metabolic syndrome, diabetes both type 1 and type 2, atherosclerosis or chronic fatigue syndrome, NASH, obesity, hepatic encephalopathy and potentially several immune mediated disorders among them Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo. The methods described herein may also be applied for the treatment of disorders associated with an abnormal or unwanted immune response associated with cell, tissue or organ transplantation, e.g., renal, hepatic, and cardiac transplantation, e.g., graft versus host disease (GVHD), or to prevent allograft rejection, by altering various pathways using the capsule. Each possibility represents a separate embodiment of the present disclosure.

For any type of the above-described stimuli that can be applied by the gastrointestinal capsule of the present disclosure, durable effect can be achieved by randomness of the parameters of the stimuli, namely, by randomly-altering the parameters of the stimuli during operation of the capsule, for example, in terms of intensity and frequency. Without being bound by any particular theory or mechanism of action, the randomness of the stimulation parameters may change the type of mechanism underlying a physiological effect achieved by the capsule, and may enable overcoming any type of tolerance to the effect of the capsule on any of its target organs.

The capsule may be ingested with a meal, before a meal or after a meal, to optimize the desired effect. The timing for ingesting the capsule may be determined, for example, depending on the condition to be treated.

In some embodiments, the capsule according to embodiments of the present disclosure may be used for diagnostic purposes. For example, the capsule motion within the GI tract may be monitored and thus assist in locating areas of blockage or reduced motility. According to these embodiments, the capsule further comprises a recorder and/or transmitter, which is arranged to transmit the status of the capsule to an external receiver.

Thus, according to another aspect, the present disclosure provides a method for diagnosing a GI motility disorder in a subject, the method comprising inserting and activating a gastrointestinal capsule according to embodiments of the present disclosure to the GI tract of the subject, and monitoring the motion of the gastrointestinal capsule within the GI tract of said subject.

In some embodiments, the capsule according to embodiments of the present disclosure may be utilized as a delivery system for any material and substance within the alimentary canal.

Non-limiting examples of such substances include chemotherapeutic, cytotoxic anti-inflammatory and antibiotic agents. The capsule may include an activation system for release of the substance in a specific location (controlled release of the substance). Release of the substance may be remotely controlled.

In some embodiments, the stimulatory devices disclosed herein may be used in the treatment of diseases or disorders affecting the heart, brain, kidney, muscles, nerves, urinary system, lungs, liver and/or pancreas.

In some embodiments, a method is provided, for treating a clinical condition selected from the group consisting of an inflammatory disease, an infectious disease, an autoimmune disease, a metabolic disease and a malignant disease in a subject in need thereof. In some embodiments, the method comprises introducing an internal stimulatory device as disclosed herein into a target organ. In other embodiments, the method comprises affixing an external device as disclosed herein to the subject's body.

In some embodiments the capsule or the belt will prevent weight regain, and can be used as an adjunct therapy to any type of a diet, or weight loosing procedure, for prevention of the adaptation of the human body to the procedure and thus preventing the weight regain following these procedures.

In some embodiments the capsule or the belt will prevent weight regain, if being used before, in conjunction, or after the bariatric surgery, any type of weight loosing procedure including but not limited to intragastric balloons, use of gastric staples, gastric evacuation, or any other type of dietary procedures.

In some embodiments the gastrointestinal capsule or external device of are configured to induce a stimulation which is based on the data being received from the subject.

In some embodiments the gastrointestinal capsule or external device are configured to induce a stimulation which is based on pre-programmed patient's tailored algorithm which is based on body weight, BMI, metabolic, endocrine, and other physiologic parameters of the subject.

In some embodiments, the controller is configured to be pre-programmed to randomly alter a combination of parameters for which each is being altered in a random chaotic way every part of a second to every few minutes or hours.

According to some embodiments, the devices disclosed herein are characterized by chaotic dynamics (chaotic rhythm) of the stimulation, meaning that they are configured to randomly select different combinations of various types of stimuli each being altered in a random way. According to some embodiments, the chaotic/random type of combination of stimuli may be induced by different patterns, different magnitude or different rhythms of the stimuli, each of them by itself, or all together. In some embodiments, the devices described herein are configured to receive data from the target organs.

In some embodiments, the devices described herein are configured to change the algorithm based on the data being received from the target organ.

According to some embodiments the controller can generate a feedback loop based on the data it receives.

In some embodiments the gastrointestinal capsule or external device are configured to induce a stimulation which is based on pre-programmed patient's tailored algorithm which is based on body weight, BMI, metabolic, endocrine, and other physiologic parameters of the subject.

In some embodiments the capsule or the belt will prevent weight regain, and can be used as an adjunct therapy to any type of a diet, or weight loosing procedure, for prevention of the adaptation of the human body to the procedure and thus preventing the weight regain following these procedures.

In some embodiments the capsule or the belt may be utilized for preventing weight regain, if being used before, in conjunction, or after the bariatric surgery, any type of weight loosing procedure including but not limited to intragastric balloons, use of gastric staples, gastric evacuation, or any other type of dietary procedures.

In some embodiments the gastrointestinal capsule or external device of are configured to induce a stimulation which is based on the data being received from the subject.

In some embodiments the gastrointestinal capsule or external device are configured to induce a stimulation which is based on pre-programmed patient's tailored algorithm which is based on body weight, BMI, metabolic, endocrine, and other physiologic parameters of the subject.

As used herein, the statement "receive data from the organ" may refer to obtaining measurements from a sensor related to a state or function of the organ.

According to some embodiments, the device is configured to provide stimulation based on a set of parameters related to the user. According to some embodiments, the parameters may include health state, treatment goals, previous history of treatment, overall wellbeing, gender, age, weight, height, body fat percentage and more.

According to some embodiments, the device may utilize a machine-learning capability, in which the altering of the stimulation characteristics may be done for achieving low habituation based on habituation patterns and behaviors obtained from previous stimulations.

The foregoing description of the specific embodiments will so fully reveal the general nature of the disclosure that others can, by applying current knowledge, readily modify and/or adapt for various applications such specific embodiments without undue experimentation and without departing from the generic concept, and therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed chemical structures and functions may take a variety of alternative forms without departing from the disclosure.

According to some embodiments, the randomness of stimulation altering (chaotic stimulation) may be achieved by chaotically/randomly altering stimulation characteristics per stimulation technique, randomly/chaotically altering between different techniques/mechanisms of stimulation, utilizing multiple stimulation techniques at a given time or any combination thereof.

EXAMPLES

Example 1

Mice: 4 C57BL, Males, 12 Weeks Old

Following a 12 hours fast, one group of mice was exposed to 5 minutes of external body stimulation or and another group was not exposed to stimulation to serve as a control group. The stimulation was delivered using an external rotor attached to their upper abdomen. The Gherlin levels of the Mice were measured/tracked. The measurements were done as follows:

| Time | Action |
| --- | --- |
| 0 | Draw blood for hormones |
| 5 min rotator on abdomen | Draw blood for hormones |

Preparation of the Samples:

Blood was drawn into anti-coagulant containing tubes, and AEBSF was added to stabilize the Ghrelin hormone, to a final concentration of 1 mg/ml., let clot for 30 min. Centrifuge at 2000-3000 g for 15 min at 4 C. Take the serum to new tubes. Acidify with HCl to a final concentration of 0.05 N. The samples are ready for the Ghrelin assay.

Figure 9:
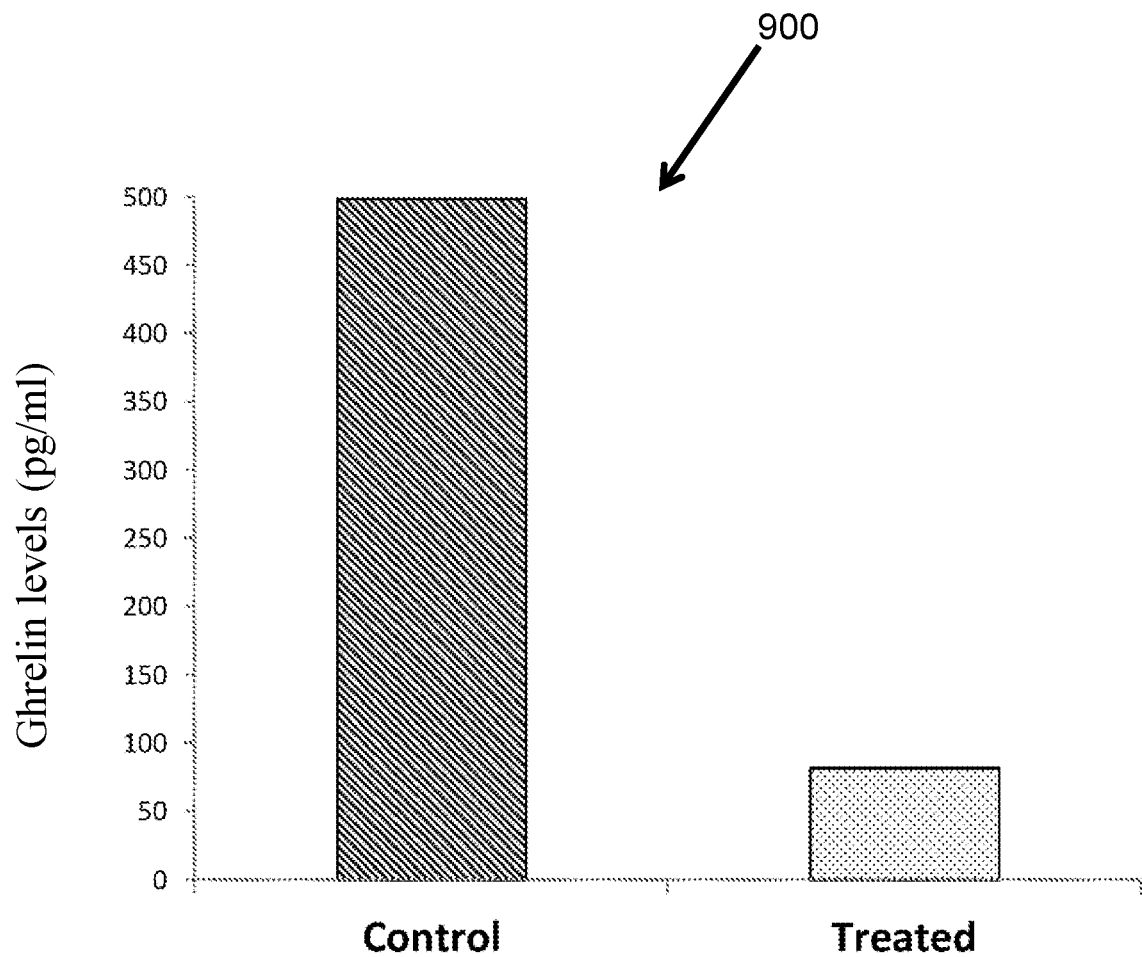
FIG. 9 depicts a first experiment result, according to some embodiments.

Reference is now made to FIG. 9, which depicts a first experiment result 900, according to some embodiments. Results 900 show a reduction in ghrelin levels following 5 minutes of external body stimulation compared with control from 499 to 82 pg/ml respectively. The data suggests that external gastric stimulation can reduce ghrelin levels.

Example 2

Mice: 4 C57BL, Males, 12 Weeks Old

Following a 12 hours fast, some mice were exposed to 5 minutes of external body stimulation while others were exposed to no stimulation, forming a control group. The stimulation was applied using an external rotor attached to the upper abdomen of the mice, one group thereof was stimulated in in a regular manner, while the other group was stimulated in an irregular chaotic way.

The Gherlin levels of the Mice were measured/tracked. The measurements were done as follows:

| Time | Action |
| --- | --- |
| 0 | Draw blood for hormones |
| 5 min rotator on abdomen | Draw blood for hormones |

Preparation of the Samples:

Blood was drawn into anti-coagulant containing tubes, and AEBSF was added to stabilize the Ghrelin hormone, to a final concentration of 1 mg/ml., let clot for 30 min. Centrifuge at 2000-3000 g for 15 min at 4 C. Take the serum to new tubes. Acidify with HCl to a final concentration of 0.05 N. The samples are ready for the Ghrelin assay.

Figure 10:
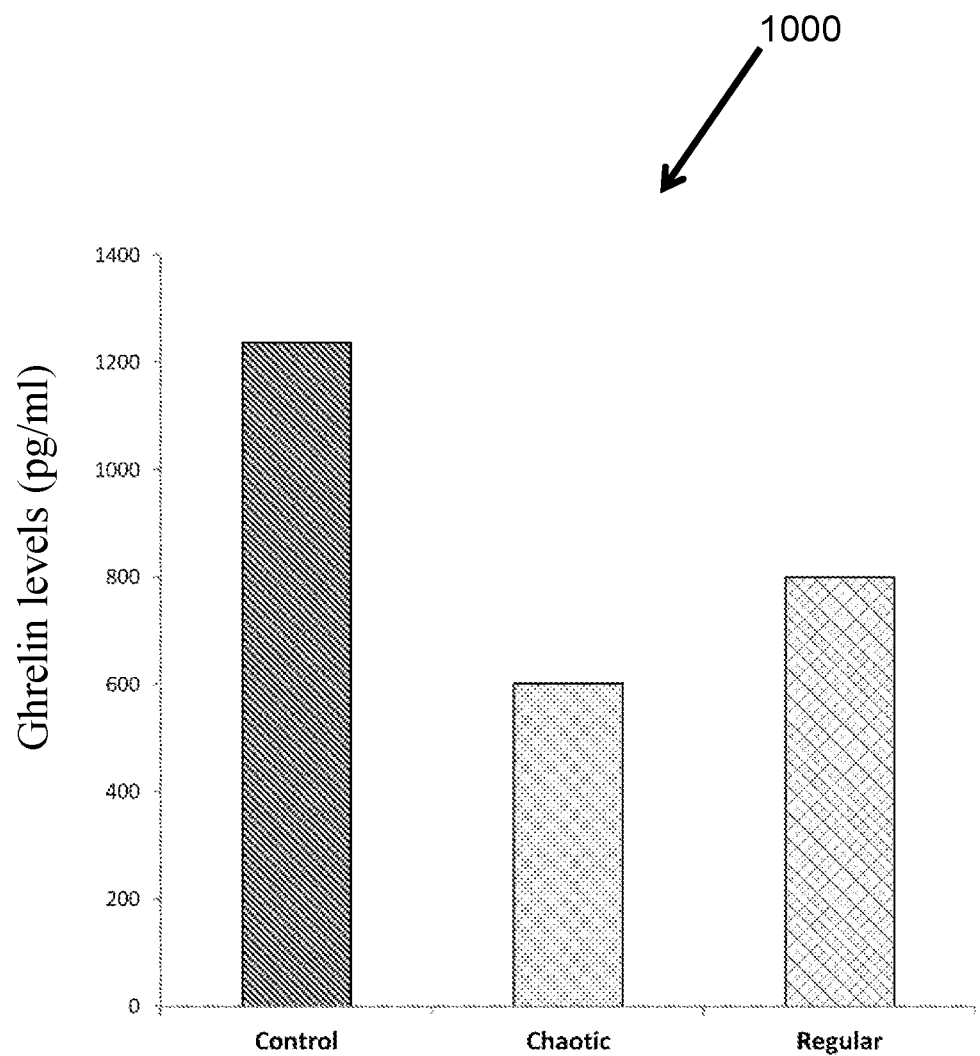
FIG. 10 depicts a second experiment result, according to some embodiments.

Reference is now made to FIG. 10, which depicts a second experiment result 1000, according to some embodiments. Results 1000 show a reduction in ghrelin levels following 5 minutes of external body stimulation compared with control from 1237 to 800 pg/ml respectively using regular rhythm. However using an irregular chaotic rhythm ghrelin levels further decreased to 602 pg/ml. The data suggests that irregular chaotic external gastric stimulation has a better effect on reducing ghrelin levels.

Example 3

Mice: 4 C57BL, Males, 12 Weeks Old

Following a 12 hours fast, some mice were exposed to 5 minutes of external body stimulation, and others were exposed to no stimulation, forming a control group. The stimulation was applied using an external rotor attached to the upper abdomen of the mice, and one group of mice received stimulation in a regular manner, while another group received stimulation in an irregular chaotic way.

The Gherlin levels of the Mice were measured/tracked. The measurements were done as follows:

| Time | Action |
| --- | --- |
| 0 | Draw blood for hormones |
| 5 min rotator on abdomen | Draw blood for hormones |

Preparation of the Samples:

Blood was drawn into anti-coagulant containing tubes, and AEBSF was added to stabilize the Ghrelin hormone, to a final concentration of 1 mg/ml., let clot for 30 min. Centrifuge at 2000-3000 g for 15 min at 4 C. Take the serum to new tubes. Acidify with HCl to a final concentration of 0.05 N. The samples are ready for the Ghrelin assay.

Figure 11:
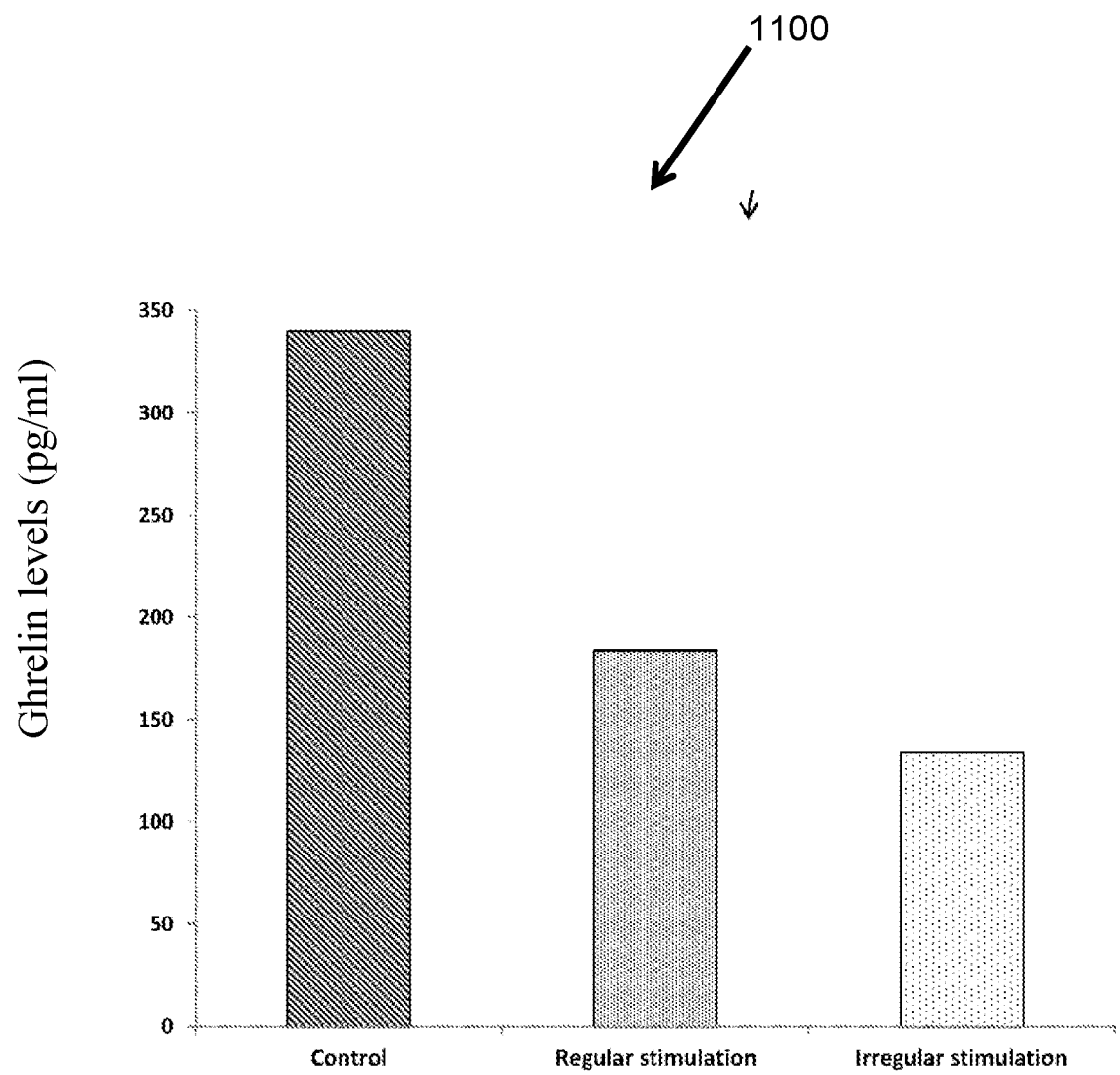
FIG. 11 depicts a third experiment result, according to some embodiments.

Reference is now made to FIG. 11, which depicts a third experiment result 1100, according to some embodiments. Results 1100 show a reduction in ghrelin levels following 5 minutes of external body stimulation compared with control from 340 to 184 pg/ml respectively using regular rhythm. However, using an irregular chaotic rhythm ghrelin levels further decreased to 134 pg/ml. The data suggests that irregular chaotic external gastric stimulation has a better effect on reducing ghrelin levels.

The invention claimed is:

1. A gastrointestinal capsule comprising a capsule body comprising a control circuitry, and an inflatable-deflatable balloon functionally attached to said capsule body, said balloon is operative to inflate and/or deflate in response to a command from the control circuitry, to thereby apply a mechanical stimulation to a gastrointestinal wall of a subject; wherein the capsule is configured to apply a mechanical stimulation through the inflatable-deflatable balloon; wherein the control circuitry is configured to randomly alter the volume of the balloon between values ranging from about 10 ml to about 2000 ml, wherein the capsule is further configured to apply a mechanical stimulation through rotation thereof and wherein the capsule body further includes a stimuli delivery mechanism configured to induce stimulation selected from a group consisting of mechanical stimuli, electrical stimuli and thermal stimuli.

2. The gastrointestinal capsule of claim 1, wherein the stimulation is a mechanical stimuli, and the mechanical stimuli is configured to be applied through vibration of the capsule, and wherein the control circuitry is configured to randomly alter the vibration frequency between values within a physiological range.

3. The gastrointestinal capsule of claim 2, wherein the control circuitry is configured to obtain a signal indicative of a state or operation of the gastrointestinal wall of the subject from a sensor, and generate stimuli based on the obtained signal.

4. The gastrointestinal capsule of claim 2, wherein the control circuitry is configured to randomly alter the vibration frequency between values below and above physiological values.

5. The gastrointestinal capsule of claim 2, wherein the control circuitry is configured to randomly alter the vibration frequency between values ranging from about 0.01 to about 10,000 Hertz (Hz).

6. The gastrointestinal capsule of claim 1, wherein the capsule is configured to generate a local temperature alteration in the immediate surroundings of the gastrointestinal capsule when the capsule is activated inside a gastrointestinal tract of a subject.

7. The gastrointestinal capsule of claim 1, configured to induce a continuous stimulation, an intermittent random or a chaotic stimulation.

8. The gastrointestinal capsule of claim 1, configured to induce a random combination of stimuli, each being delivered with random alteration of stimulation characteristics.

9. The gastrointestinal capsule of claim 1, wherein the capsule is configured to commence activation thereof after a defined time-period following ingestion thereof, such that the capsule is activated as it reaches a target segment within the gastrointestinal (GI) tract.

10. The gastrointestinal capsule of claim 1, wherein the capsule further comprises one or more arms configured to extend and anchor the capsule at a selected location within the gastrointestinal (GI) tract.

11. The gastrointestinal capsule of claim 1, wherein the control circuitry is configured to randomly alter the rotation frequency between values ranging from about 10,000 cycles/second to about 1 cycle/minute.

12. The gastrointestinal capsule of claim 1, wherein the capsule is configured to apply an electrical stimulation.

13. The gastrointestinal capsule of claim 12, wherein the control circuitry is configured to alter the frequency of the electrical stimulation between values ranging from about 0.00001 Hz to about 10000 Hz and/or the pulse intensity of the electrical stimulation between values ranging from about 0.01 milliamps (MA) to about 10000 mA.

14. A method for preventing weight regain, the method comprising:
    introducing the gastrointestinal capsule of claim 1 into a gastrointestinal tract of a subject;
    configuring the capsule to apply a mechanical stimulation through the inflatable-deflatable balloon, to the gastrointestinal tract wall when activated inside the gastrointestinal tract, and further configured to apply a mechanical stimulation through rotation of the capsule;
    activating said capsule for providing the mechanical stimulation thereby habituation effect to the stimulation.

15. The gastrointestinal capsule of claim 1, wherein the volume of the balloon is configured to be randomly altered between values ranging from about 300 ml to about 800 ml.

16. The gastrointestinal capsule of claim 1, wherein the volume of the balloon is configured to be randomly altered between values ranging from about 400 ml to about 700 ml.

17. The gastrointestinal capsule of claim 1, wherein said inflating and/or deflating of the balloon is controlled via a pump.

18. The gastrointestinal capsule of claim 17, wherein the pump is configured to pump gas and/or liquid in and from the balloon.

19. The gastrointestinal capsule of claim 18, further comprising a gas container, wherein the pump and the balloon are connected to the gas container.

* * * * *